(12) United States Patent
Ball et al.

(10) Patent No.: US 6,340,569 B1
(45) Date of Patent: Jan. 22, 2002

(54) MONOCLONAL ANTIBODY AND ANTIGENS SPECIFIC THEREFOR AND METHODS OF USING SAME

(75) Inventors: Edward D. Ball; Rui-Kun Zhong, both of San Diego, CA (US)

(73) Assignee: University of Pittsburgh, Pittsburgh, PA (US)

(*) Notice: Subject to any disclaimer, the term of this patent is extended or adjusted under 35 U.S.C. 154(b) by 0 days.

(21) Appl. No.: 09/189,926

(22) Filed: Nov. 12, 1998

Related U.S. Application Data

(60) Provisional application No. 60/066,906, filed on Nov. 14, 1997, and provisional application No. 60/065,503, filed on Nov. 12, 1997.

(51) Int. Cl.$^7$ .................. G01N 33/53; C12Q 1/02; C12N 5/06; C12N 5/08; C07K 16/28
(52) U.S. Cl. .................. 435/7.2; 435/29; 435/325; 435/326; 435/372.2; 530/388.7; 530/388.73
(58) Field of Search .................. 435/325, 326, 435/372.2, 7.2, 29; 530/388.7, 388.73

(56) References Cited

U.S. PATENT DOCUMENTS

| | | |
|---|---|---|
| 5,407,805 A | 4/1995 | Seon |
| 5,441,871 A | 8/1995 | Seon |
| 5,464,753 A | 11/1995 | Chaudhary et al. |
| 5,475,063 A | 12/1995 | Kaplan et al. |
| 5,583,033 A | 12/1996 | Terstappen et al. |
| 5,629,009 A | 5/1997 | Laurencin et al. |
| 5,644,033 A | 7/1997 | Seon |
| 5,700,691 A | 12/1997 | Bender et al. |
| 5,747,034 A | 5/1998 | De Boer et al. |
| 5,773,293 A | 6/1998 | Kilgannon et al. |
| 5,788,963 A | 8/1998 | Murphy et al. |
| 5,804,446 A | 9/1998 | Cerami et al. |
| 5,807,715 A | 9/1998 | Morrison et al. |
| 5,821,332 A | 10/1998 | Godfrey et al. |

FOREIGN PATENT DOCUMENTS

| | | |
|---|---|---|
| WO | WO 94/02156 | 2/1994 |

OTHER PUBLICATIONS

Waalen, K et al. Scand. J. Rheumatol. Suppl. 76:47–60, 1988.*
Freudenthal, PS et al. Internat. Rev. Immunol. 6(2–3):103–116, 1988.*
Steinman, R.M. et al. Identification of a novel cell type in peripheral lymphoid organs of mice. I. Morphology, quantitation, tissue distribution. J. Exp. Med. May 1, 1973; 137(5):1142–62.
Steinman, R.M. et al. Identification of a novel cell type in peripheral lymphoid organs of mice. III. Functional properties in vivo. J. Exp. Med. Jun. 1, 1974; 139(6):1431–45.
Kohler, G. et al. Continuous cultures of fused cells secreting antibody of predefined specificity. Nature. Aug. 7, 1975; 256(5517):495–97.
Steinman, R.M. et al. Lymphoid dendritic cells are potent stimulators of the primary mixed leukocyte reaction in mice. Proc. Natl. Acad. Sci. USA Oct. 1978; 75(10):5132–36.
Inaba, K. et al. Clustering of dendritic cells, helper T lymphocytes and histocompatible B cells during primary antibody responses in vitro. J. Exp. Med. Sep. 1, 1984; 160(3):858–76.
Witmer, M.D. et al. The anatomy of peripheral lymphoid organs with emphases on accessory cells: light microscopic immunocytochemical studies of mouse spleen, lymph node and Peyers patch. Am. J. Anat. Jul. 1984; 170(3):465–81.
Ball, E.D. et al. Expression of antigens associated with small call carcinoma of the lung on hematopoietic progenitor cells. Cancer Res. Dec. 15, 1987; 47(24 Pt 1):6556–59.
Corradi, M.P. et al. Development of a cell with dendritic morphology from a precursor of B lymphocyte lineage. J. Immunol. Apr. 1, 1987; 138(7):2075–81.
Cerny, A. et al. Development of follicular dendritic cells in lymph nodes of B–cell–depleted mice. Cell Tissue Res. Nov. 1988; 254(2):449–54.
Hart, D.N. et al. Isolation and characterization of human tonsil dendritic cell. J. Exp. Med. Jul. 1, 1988; 168(1):157–70.
Freudenthal, P.S. et al. The distinct surface of human blood dendritic cells, as observed after an improved isolation method. Proc. Natl. Acad. Sci. USA Oct. 1990; 87(19):7698–702.
Steinman, R.M. The dendritic cell system and its role in immunogenicity. Annu. Rev. Immunol. 1991; 9:271–96.
Galy A. et al. Human T, B, natural killer, and dendritic cells arise from a common bone marrow progenitor cell subset. Immunity. Oct. 1995; 3(4):459–73.
Zhou, L.J. et al. Human blood dendritic cells selectively express CD83, a member of the immunoglobulin superfamily[1]. J. Immunol. Apr. 15, 1995; 154(8):3821–35.
Borrello, M.A. et al. The B/macrophage cell: an elusive link between CD5+ B lymphocytes and macrophages. Immunol Today. Oct. 17, 1996; 17(10):471–75.
Serreze, D.V. et al. B lymphocytes are essential for the initiation of T cell–mediated Autoimmune Diabetes: analysis of a new "speed congenic" stock of NOD.Ig mu null mice. J Exp Med Nov. 1, 1996; 184(5):2049–2053.
Bates, E.E. et al. Identification and analysis of novel member of the ubiquitin family expressed in dendritic cells and mature B cells. Eur. J. Immunol. Oct. 1997; 27(10):2471–77.
Hart, D.N. Dendritic cells; Unique leukocyte populations which control the primary immune response. Blood. Nov. 1, 1997; 90(9):3245–87.

* cited by examiner

*Primary Examiner*—Christina Y. Chan
*Assistant Examiner*—F. Pierre VanderVegt
(74) *Attorney, Agent, or Firm*—Reed Smith LLP

(57) ABSTRACT

Disclosed herein are hybridomas, antibodies produced thereby, antigens, and cells identified or isolated therewith. The dendritic like cells preferably have dendritic morphology and B cell phenotype. Methods of utilizing the hybridomas, antibodies, antigens, and cells are also discussed herein.

3 Claims, 18 Drawing Sheets

MONOCLONAL ANTIBODY AND ANTIGENS SPECIFIC THEREFOR AND METHODS OF USING SAME

This non-provisional application claims the benefit under 35 U.S.C. 119(e) of U.S. provisional applications 60/065,503 filed Nov. 12, 1997 and 60/066,906 filed Nov. 14, 1997.

FIELD OF THE INVENTION

The present invention relates generally to hybridomas capable of producing antibodies, even more particularly to antibodies specific for cell surface antigens, and even more particularly to the methods for utilizing the antibodies, the cells they identify, and the antigens with which they interact.

BACKGROUND OF THE INVENTION

The immune system is crucial for survival, as it initiates the destruction and elimination of both invading organisms (e.g., a virus) and toxic materials produced by such organisms. There are two broad types of immune system responses: (1) "antibody" responses; and (2) "cell mediated" responses. Antibodies circulate in the bloodstream and permeate other body fluids and tissues. Antibodies generally bind with specificity to the antigens which induced the antibody response. This binding works to both inactivate the antigen as well as aid in the destruction of the antigen. The cell mediated response involves the production of specialized cells which react with antigens on the surface of virus-infected host cells. These specialized cells work to destroy the virus-infected host cell before the virus is able to replicate and further infect other cells.

The cells involved in the immune system response are a class of white blood cells referred to as "lymphocytes." These lymphocytes are generally classified into two types: "B cells" and "T cells." B cells are generally described as having "receptors" which can "recognize" an antigen alone, leading to production of antibodies specific for the recognized antibody. T cells, on the other hand, are known to have receptors which cannot recognize an antigen unless it is associated with cell-membrane proteins referred to as "major histocompatability complex" (MHC) molecules. There are generally two classes of MHC molecules, referred to as "class I" and "class II". In the cell mediated response, the antigen is degraded by the cell, forming small peptide fragments that form physical complexes with a "class I" or "class II" MHC molecule. The peptide-class I or peptide-class II MHC complex is then exported to the surface of the cell, and this complex is then capable of being recognized by T cells.

Dendritic cells (DCs) are a diverse population of morphologically similar cell types found in a variety of lymphoid and non-lymphoid tissue. Most dendritic cells are potent antigen-presenting cells specialized in initiating primary T cell immune responses. Dendritic cells generally have long, tentacle-like projections which express high levels of class II MHC molecules. Dendritic cells represent less than 0.1% of white blood cells (these are referred to as "blood dendritic cells"). Dendritic cells are also found in lymphoid organs (such as the tonsil) and are referred to as "interdigitating dendritic cells" when associated with T cell areas (e.g., lymphoid organs), and "follicular dendritic cells" when associated with B cell areas. They are also known as veiled cells present in afferent lymph, as Langerhans cells in the epidermis and as dermal DCs in the dermis of the skin. One function for dendritic cells is capturing antigens and stimulating T cell response. In essence, dendritic cells "pick-up" antigens and migrate the captured antigens to T cells. Because dendritic cells can induce a T cell response to an antigen without other adjuvants, DCs are often referred to as "nature's adjuvant." As "nature's adjuvant," dendritic cells have attracted attention for therapeutic purposes.

PCT Publication WO 94/02156 purportedly describes a method for isolating human DCs to present antigens to induce antigen specific T cell mediated responses. Uses mentioned include cellular immunotherapy and cancer treatment. U.S. Pat. No. 5,788,963 purportedly teaches methods and compositions for use of human dendritic cells to activate T cells for immunotherapeutic response against primary and metastatic prostrate cancer cells.

SUMMARY OF THE INVENTION

An embodiment of the present invention relates to kits, e.g., diagnostic assay kits, utilizing the antibody to tumor-associated antigens and carrying out the method disclosed here.

An embodiment of the present invention may be described as a hybridoma formed by fusion of a tumor cell and a non-tumor cell, more specifically, lymphocytes and tumor cells. The hybridoma provides continuously replicating (hybrid) cells which exhibit some or all the characteristics of the non-tumor cell. The hybridomas of the present invention are used to produce or secrete antibodies which interact with cells having a dendritic morphology. Preferably, the monoclonal antibodies of the present invention produced by the hybridomas recognize cells having both a dendritic morphology and a B cell phenotype. Even more preferably the hybridoma is specific for cells which are defined herein as B-DC cells. A hybridoma in accordance with the present invention has been deposited with the American Type Culture Collection (A.T.C.C.) and has an A.T.C.C. Accession Number HB-12430 (reported with the A.T.C.C. 10801 University Boulevard, Manassas, Va. 20110-2209; U.S.A., U.S.A., Nov. 14, 1997, determined viable by the A.T.C.C. on Nov. 18, 1997).

Another embodiment of the present invention is a hybridoma comprised of lymphocytes and tumor cells wherein at least a portion of the lymphocytes and tumor cells are fused to form a hybridoma capable of producing antibodies. The antibodies preferably recognize a 220 kDa protein on the surface of cells. The 220 kDa protein located on the cells is recognized by the antibodies produced by the hybridoma and is further capable of being reduced to four subunits which consist of about 55 kDa, about 65 kDa, about 80 kDa, and about 85 kDa subunits. It is preferable that the 220 kDa protein be an antigen, and that the hybridoma be designated hybridoma 5G9 with A.T.C.C. Accession Number HB-12430. The monoclonal antibody expressed by hybridoma 5G9 (mAb 5G9) is a preferred embodiment capable of reacting with cells expressing the 220 kDa protein. It is to be understood that other monoclonal antibodies having substantially the same function (i.e., able to recognize 220 kDa proteins) are encompassed within the scope of the present invention.

Another embodiment of the present invention is a monoclonal antibody or fragment thereof which is capable of reacting with cells expressing a protein on the surface of the cell which is indicative of the cells' morphology, preferably a dendritic like morphology. As discussed above, it is preferable that the antibodies are produced by a hybridoma cell line, most preferably hybridoma cell line 5G9, having A.T.C.C. Accession N HB-12430, or subclones thereof. It is preferable that the monoclonal antibody of this embodiment react with specific lymphoma cells, even more preferably lymphoma cells known as chronic lymphocitic leukemia cells.

Another embodiment of the present invention is a cell which is isolated from a blood cell population wherein the cell expresses the 220 kDa protein discussed above. It is more preferable that the cell expresses the protein on the surface of the cell. It is also preferred that the cell which is isolated have a dendritic morphology and even more preferably also a B-cell phenotype. Additionally, it is preferable that the cell have a function which is similar to that of classic dendritic cells. More preferably the cells react with the monoclonal antibody 5G9 or a monoclonal antibody specific for the 220 kDa cell surface protein. It is even more preferable that the cell be isolated from peripheral blood mononuclear cells and even more preferable that the cell express a phenotype which is selected from the group CD19+, CD20+, CD40+, CD83+ (after positive selection), HLA-D- hi positive, immunoglobulin $\mu$ chain positive, Kappa light chain positive, lamda-light chain positive, CD3-, CD4-, CD5-, CD10-, CD13-, CD14-, CD15-, CD16-, CD33-, CD56-, CD64-, and any combination of one or more of the above phenotypes. Even more preferably the phenotype is selected from the group consisting of CD4-, CD33-, and both CD4- and CD33-. As used herein, cell morphology generally refers to the processes and preferably long and thin processes, of the cells which give rise to classical morphological association with dendritic cells.

Another embodiment of the present invention is a method of identifying an antigen presenting cell which is comprised of exposing the population of cells to a monoclonal antibody, preferably monoclonal antibody mAb 5G9. In this method it is preferable that mAb 5G9 be secreted by a hybridoma designated 5G9 (A.T.C.C. Accession Number HB-12430) and that the antigen presenting cell have a phenotype selected from the group above, and even more preferable that the phenotype be selected from the group CD4-, CD33-, and both CD4- and CD33-.

Another embodiment of the present invention is an enriched cell population which is comprised of cells expressing a predetermined protein or antigen. It is preferred that the enriched population of cells have a proportion of cells having a dendritic morphology, and that the cells having a dendritic morphology appear in a higher concentration or higher purity in the enriched population than that which is endogenous for naturally occurring cell sources to which it is being compared. It is preferable that the cells having a dendritic morphology have a B cell phenotype in that they also function similar to dendritic cells. It is even more preferable that the enriched population have a portion of cells which react with monoclonal antibody 5G9 (mAb 5G9) and more preferably that they be isolated from peripheral blood mononuclear cells. As discussed herein, it is preferable that at least a portion of an enriched population of cells exhibit long and thin processes similar to dendritic cells. With regard to the protein or antigen it is preferred that the 220 kDa protein is capable of being reduced to four subunits, specifically subunits of about 55, 65, 80 and 85 kDa.

Another embodiment of the present invention is an isolated antigen presenting cell having dendritic cell properties and characteristics. In this embodiment of the present invention, the antigen presenting cells preferably have a morphology and function similar to that of classic dendritic cells. It is preferred that the antigen presenting cells of this embodiment be reactive with a monoclonal antibody, preferably monoclonal antibody 5G9 (mAb 5G9). It is also preferable that the antigen presenting cell be a peripheral mononuclear cell which expresses a phenotype as described above and preferably a CD83+ (after positive selection) phenotype.

Another embodiment of the present invention is a therapeutic composition which is comprised of an antigen presenting cell wherein said antigen presenting cell has dendritic cell properties and characteristics and a substantially similar function. It is preferable that the antigen presenting cell of the therapeutic composition be reactive with monoclonal antibody 5G9 (mAb 5G9) or a similar antibody which is specific for a 220 kDa protein located on the surface of a cell. As above, it is preferable in a therapeutic composition that the antigen presenting cell express a phenotype selected from the group CD19+, CD20+, CD40+, CD83+ (after positive selection), HLA-D- hi positive, immunoglobulin $\mu$ chain positive, Kappa light chain positive, lamda-light chain positive, CD3-, CD4-, CD5-, CD10-, CD13-, CD14-, CD15-, CD16-, CD33-, CD56-, CD64-, and any combination of one or more of the above phenotypes, and even more preferably that the composition include an antigen presenting cell.

Another embodiment of the present invention is a method of treating a mammal which is comprised of administering a therapeutically effective amount of a B-DC cell to the mammal, wherein the B-DC cell has both B cell phenotype and dendritic cell morphology.

Another embodiment of the present invention is a method of isolating dendritic like cells comprising reacting a population of cells with a monoclonal antibody, preferably monoclonal antibody 5G9. In this embodiment it is preferable that the cells which are to be isolated have a morphology similar to the dendritic cell, functions similar to the dendritic cell and that the cells are reactive therewith.

Another embodiment of the present invention is a method of initiating a therapeutic response which is comprised of administering to a patient an effective amount of a cell having a B cell phenotype and a dendritic cell morphology (i.e., a B-DC cell). Yet another embodiment of the present invention is a method of isolating cells having dendritic like morphology comprised of obtaining a cell sample which contains the cells having dendritic like morphology and mixing a sample of the monoclonal antibody capable of reacting with the antigen expressed by the dendritic like cells. It is preferable that monoclonal antibody have a recognition characteristic similar to that of monoclonal antibody 5G9 in that it recognizes a cell-surface antigen preferably a self-servicing antigen comprised of a 220 kDa protein. After the samples are mixed, the cells are selected so as to separate from the sample a substantially pure population of cells having dendritic like characteristics, preferably both with a dendritic like characteristic and B cell type phenotype.

In one embodiment, the diagnostic kit would conventionally include the monoclonal antibody mAb 5G9 in one or more containers, a conjugate of a specific binding partner for the antibody, a label capable of producing a detectable signal, and instructions for its use. The kit may be conjugated to a label, as is well known to the art. Various labels include enzymes, radioisotopes, particulate labels, chromogens, fluorescers, chemoluminescers, coenzymes, free radicals, and bacteriophages. Additionally the antibody may be bound to a support. The instructions for use are suitable to enable an end user to carry out the desired test. By the term "instructions for use," it is meant a tangible expression describing the reagent concentration for at least one assay method, parameters such as the relative amount of reagent and sample to be admixed, maintenance time periods for reagent/sample admixtures, temperature, buffer conditions and the like. It is within the scope of this invention to provide manual test kits or test kits for use in automated analyzers.

Specific preferred embodiments of the present invention will become apparent from the following Figures, detailed description examples and claims.

DETAILED DESCRIPTION OF THE INVENTION

Figure 1:
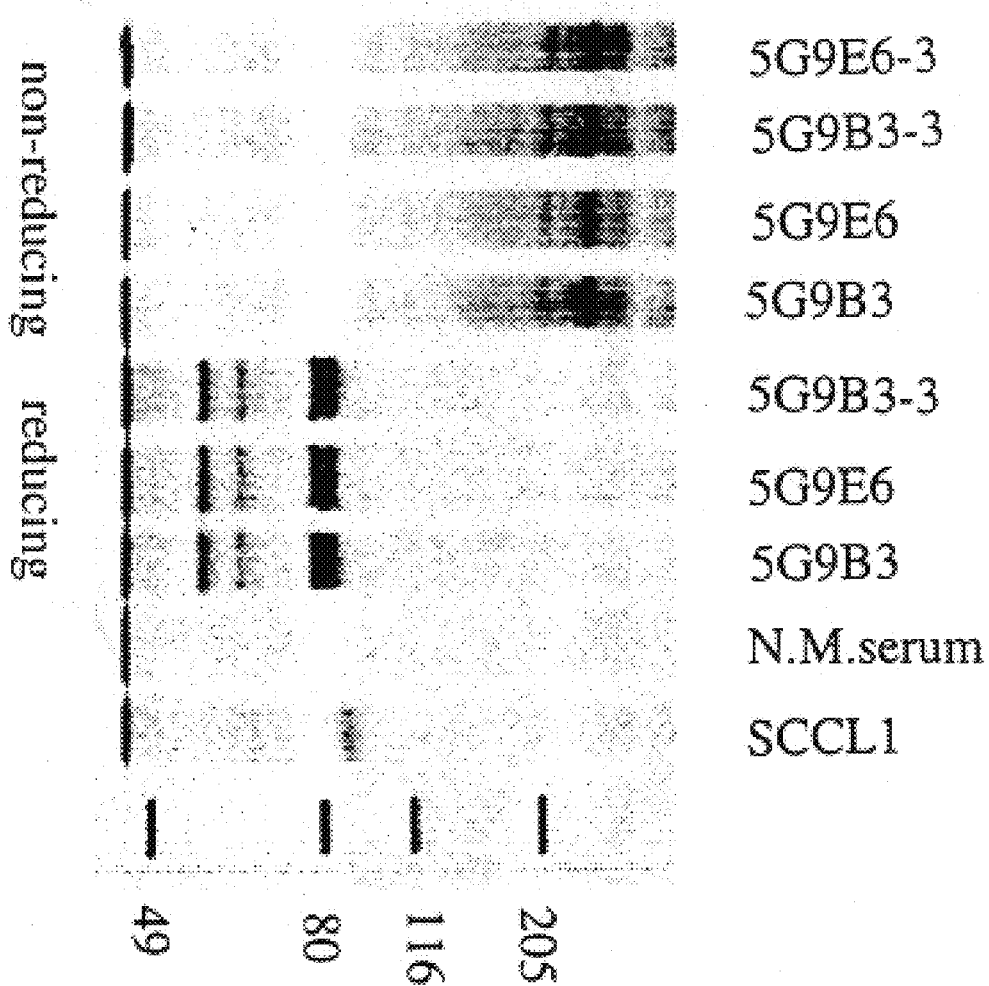
FIG. 1 is a reproduction of a Western blot immunoprecipitation analysis of binding of mAb 5G9 (subclones).

The present invention relates to the identification of a population of cells that express a unique surface antigen to a monoclonal antibody produced by a hybridoma disclosed herein. In particular, the present invention relates to the isolation, characterization and uses of these hybridomas, antibodies, antigens, and cells associated therewith. The cells of the present invention can be distinguished from other cells by their size, morphology, cell surface phenotype and biological activities. These hybridomas, antibodies, antigens, and cells may have a wide range of applications, including, but not limited to modulation (i.e., stimulation or depression) of the immune system, gene therapy, diagnostic kits and cell identification, isolation and purification.

The term "immunogen" as used herein refers to any substance, such as a molecule, cell, virus or fragment of such molecule, cell or virus which can be administered to an individual in an effort to elicit an immune response. The term "immunogen" thus simply refers to such substances which are or can be administered or otherwise used to raise antibodies or cellular immune system components, such as by "priming". When used in connection with "immunogen", the term "molecule" refers to a molecule or molecular fragment of the antigen. Likewise when used to refer to a cell, virus or fragment thereof, the immunogen can be the cell, virus or component thereof, which can be introduced to cells to modify or modulate the immune response thereby. The term "immunogen" therefore encompasses antigenic materials such as cells, viruses, cellular and viral components, antigenic compounds, and foreign proteins.

The term "antigen" refers to substances, e.g., molecules which induce an immune response. It thus can refer to any molecule contacted by the immune system, and may include without limitation, proteins, nucleic acids and the like. Each antigen typically comprises one or more epitopes.

The term "antibody" refers to immunoglobulins, including whole antibodies as well as fragments thereof that recognize or bind to specific epitopes. An antibody "preparation" thus contains such antibodies or fragments thereof, which are reactive with an antigen when at least a portion of the individual immunoglobulin molecules in the preparation recognize (i.e., bind to) the antigen. An antibody is said to "recognize" an epitope if it binds to the epitope. Hence, "recognition" involves the antibody binding reaction with an epitope, which may include the typical binding mechanisms and methods. "Binding" is thus used in the conventional sense, and does not require the formation of chemical bonds. "Fragments" as used herein means a section of a larger intact antibody, which section continues to contain desired recognition sequences. Such fragments in that sense may, in themselves, be considered antibodies and the term "antibody" may be considered to include such fragments.

The term "epitope" is used to identify one or more portions of an antigen or an immunogen which is recognized or recognizable by antibodies or other immune system components. The "epitope region", as used herein, refers to the epitope and the surrounding area in the vicinity of the epitope, taking into account three dimensional space. Hence, this may take into account the tertiary and quaternary structure of the antigen.

"Processing" and "presentation" refer to the mechanisms by which the antigen is taken up, altered and made available to the immune system. Presentation also includes, when appropriate, complexation or binding with MHC. In certain instances, processing entails the uptake and partial proteolytic degradation of the antigen by antigen presenting cells, as well as display on the antigen presenting cells surface in the context of MHC. The terms "reaction" and "complex" as well as derivatives thereof, are used in the general sense, and are not to be construed as requiring any particular reaction mechanism or sequence.

The invention is discussed in more detail below, for purposes of description and not by way of limitation. The specific procedures and methods described and exemplified are merely illustrative.

As used herein, the term "dendritic like cells" is a term which refers to cells having a morphology of tentacle like projections. However, the preferred definition of dendritic like cells are cells expressing the 220 kDa protein, 5G9, on its surface. Thus cells having a morphology of tentacles but not expressing 5G9 may be excluded from this preferred definition of dendritic like cells.

Most studies of human dendritic cells have focused on myeloid dendritic cells. It was recently discovered that a subpopulation of CD34$^+$ $^{lin-}$CD45RA$^+$CD10$^+$ cells give rise only to lymphoid T, B, NK and dendritic cells. Limiting dilution analysis demonstrated the existence of multipotential B/NK/DC progenitor clones in the CD34$^{hi}$ lin$^-$CD10$^+$ adult bone marrow cell population, indicating that nonprimitive progenitors for lymphoid cells and for dendritic cells can be distinct from those of myeloid. This implies that the dendritic cell lineage is developmentally more closely related to the lymphoid than the myeloid lineage. Additionally, there have also been implicit suggestions that B cells play an unrecognized role, such as functioning as potent antigen presenting cells, essential for the initial development and/or activation of T cells autoreactive with pancreatic beta cells in NOD mice. The studies suggested a close relationship between dendritic cells and B cells. The identification of B/Mφ, morphologically distinct from classical macrophages, having unique surface characteristics suggestive of their B cell origin, implies that switching can occur between subsets of distantly related cells which derived from separate lineages with specialized functions.

A preferred embodiment of the present invention is a hybridoma designated 5G9, more specifically, murine IgG1 mAb 5G9 having A.T.C.C. Accession Number HB-12430 resulting from immunization of murine Balb/c mice with Daudi cells. By western blot and immunoprecipitation, mAb 5G9 reacted with a 220 kD antigen on Daudi cells which reduced to four subunits (55, 65, 80 and 85 kDa) (hereinafter referred to as 5G9). MAb 5G9 bound to 40–60% of peripheral blood B cells, but did not bind to erythrocytes, granulocytes, platelets, T cells or NK cells. MAb 5G9 bound to the majority of B cell lymphoma cell lines, but did not react with AML or ALL cell lines. MAb 5G9 brightly stained scattered cells in human tonsil sections which had a morphology similar to dendritic cells. MAb 5G9 also stained scattered cells in cytospin slides of monocyte-derived DC (MoDC) with exceptional long membrane processes, morphologically distinct from other MoDC. By flow cytometry, these cells were CD19$^+$, CD20$^+$, and comprised 2.5±1.7% of total MoDC. MAb 5G9 reacted with a fraction of metrizamide low density mononuclear cells which represented about 17±4% of the DC-enriched population. The metrizamide low density, 5G9$^+$ cells were CD20 and CD19 positive. Positive selection of blood mononuclear cells with mAb 5G9 and sheep anti-mouse IgG Dynabeads demonstrated an enriched population of cells with long and thin plasma membrane processes. Flow cytometry analysis of these cells showed them to be CD19, CD20, CD22, CD40, HLA-Dr positive, and CD83 positive (after culture), as well as immunoglobulin μ chain positive and either kappa- or lambda-light chain positive. They did not express CD3, CD10, CD56, CD14, CD33, or CD64. Functional studies showed that these cells were potent antigen presenting cells in allogeneic mixed lymphocyte reaction (MLR) compared with 5G9$^-$PBL cells, 5G9$^-$B cells, monocytes, monocyte-derived DC, and macrophages.

Experimental results indicate that the 5G9 antigen is internalized, thus indicating it plays a role in the function of antigen presentation. Because mAb 5G9 is substantially specific for antigen presenting cells, the hybridoma is useful in producing monoclonal antibodies to the 5G9 antigen, while the antibody may be useful, e.g., in: further elucidating the characteristics of human cells, particularly in the areas of antigen presentation and development; screening and isolation of human cells from natural sources, including blood; and therapeutic applications by, e.g., determining clinically relevant antigens enhancing antigen presentation, and stimulating an immune response. Modulation of expression of the antigens may also increase or decrease the immune response, as desired. The cells identified may also be used to accomplish a therapeutic end.

As used herein, the term "subject" or "patient" means any mammal, including humans. The methods herein for use contemplate prophylactic use as well as curative use in therapy of an existing condition. As used herein, the term "therapeutic" means an agent or agents utilized to treat, combat, ameliorate, prevent or improve an unwanted condition or disease of a patient.

As used herein, the term "about" means plus or minus 10% of the numerical value of the number with which it is being used. Therefore, about 50% means in the range of 45%–55%. As used herein, the term "Dalton" (or "Da") refers to the unit of mass which is equivalent to the mass of a hydrogen atom (1.66×10$^{-24}$ gram).

As evidenced by FIG. 1, the monoclonal antibodies described herein are specific for a 220 kDa antigen (5G9) found on Daudi cells (as those in the art appreciate, the Daudi tumor cell line is unable to synthesize β$_2$-microglobulin, essential for the proper conformation of the class I MHC molecule, and therefore unable to express the class I MHC molecule). Daudi cells (2×10$^7$) were cultured for 1 hr in 5 ml of methionine- and cysteine-free medium. Labeling was initiated by adding 300 μci of [$^{35}$S] methionine -cysteine, and cells were collected after 3 hr of culture. Labeled Daudi cells were lysed by resuspending them in 500 μl of ice-cold lysis buffer [50 mM Tris-HCl, 1% Nonidet P-40, 50 mg/ml bovine serum albumin (BSA), with a mixture of protease inhibitors: 5 mM ethylenediaminetetraacetate (EDTA), 100 μg/ml phenylmethylsulfonyl fluoride (PMSF), 5 μg/ml aprotinin]. Lysates were mixed with 100 μl of normal mouse serum, and precleared with killed fixed *Staphylococcus aureus* cells which had been washed in lysis buffer. The precleared lysate was divided into 100 μl aliquots. MAb 5G9, SCCL-1 [a mouse IgG2a mAb reactive with the transferrin receptor used for positive control], and negative control antibody (normal mouse serum) were added to the aliquots of lysate and mixed for 1 hr at 4° C. Rabbit anti-mouse IgG antibody was then added and mixed for another hour. The aliquots of lysate were adsorbed to 50 μl of packed, washed protein A-sepharose. The samples were analyzed by SDS-PAGE. Western blot and immunoprecipitation protocols were obtained from *Molecular Cloning: A Laboratory Manual*, J. Sambrook et al., Cold Spring Harbor Laboratory Press, 1989 18.60–18.75, 18.26–18.56. For this example, Daudi cells were immunoprecipitated with mAb 5G9, with results being presented in FIG. 1. "SCCL1" is an anti-transferrin receptor antibody, used as a positive control. The 5G9 cell surface antigen was reduced using 100 ml DTT. Designations following "5G9" are sub-clone designations. As the results indicate, mAb 5G9 binds to an antigen on Daudi cells of about 220 kDa; when reduced, the antigen evidenced four subunits of about 55, 65, 80 and 85 kDa.

Figure 2:
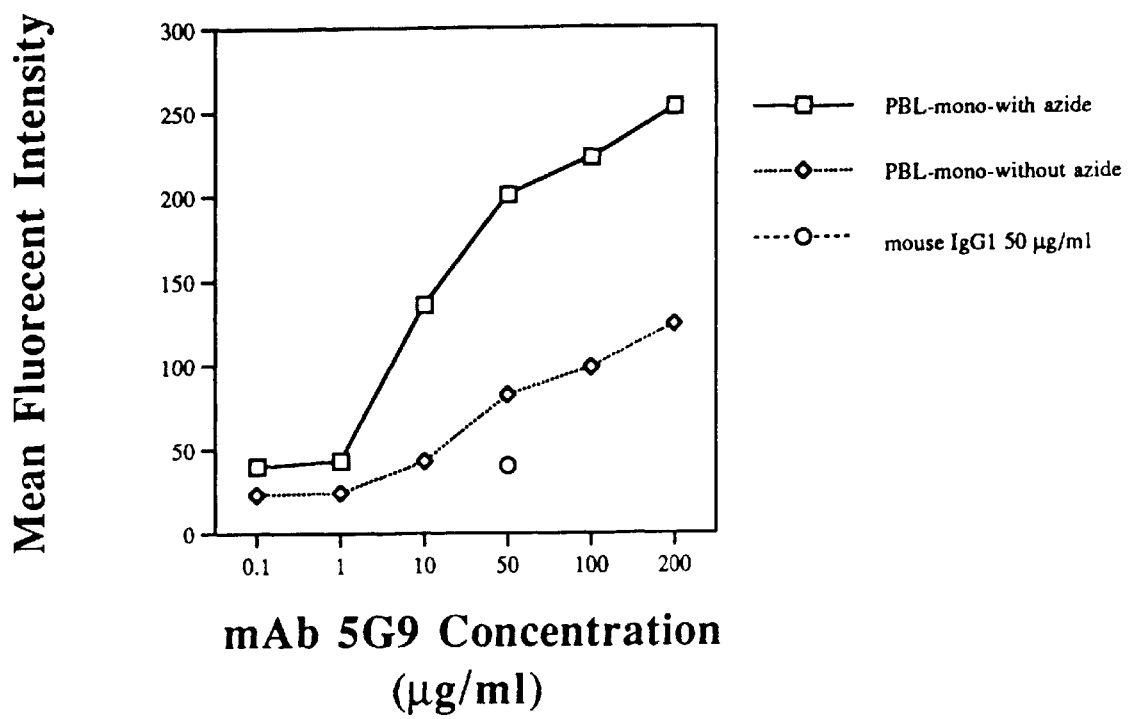
FIG. 2 is a graph measuring binding of mAb 5G9 with monocytes, with and without addition of sodium azide.
Figure 3:
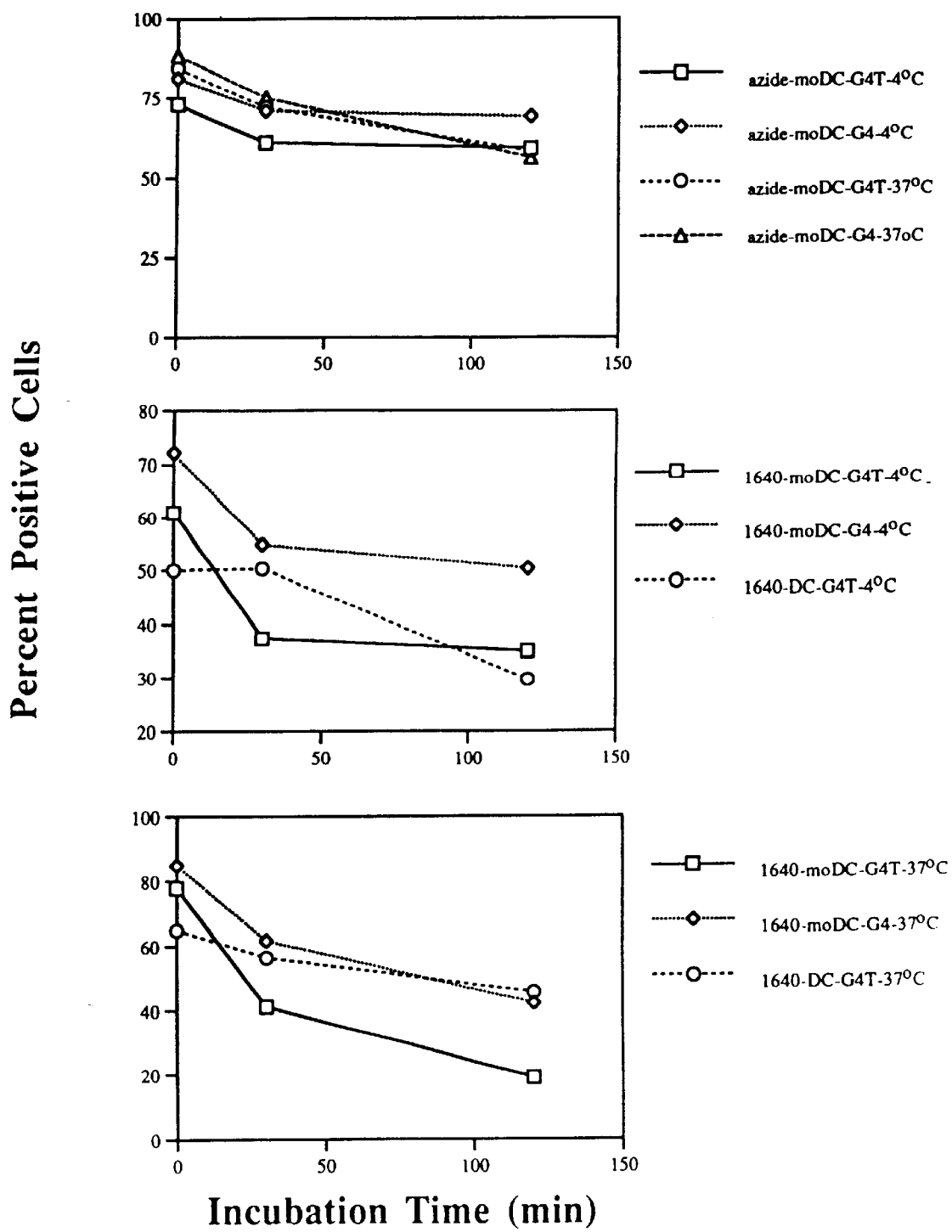
FIG. 3 is a graph illustrating binding of mAb 5G9 with monocyte-derived DCs over time.

The antibody, and the hybridoma, both referred to herein as "mAb 5G9", bind specifically with the cell surface and cytoplasm of human dendritic like cells. MAb 5G9 binds with specificity with a population or subpopulation of monocytes, dendritic cells and monocyte derived dendritic cell populations. FIG. 2 is a graph measuring binding of mAb 5G9 with monocytes (with and without addition of sodium azide) in the absence of sodium azide, mean fluorescence intensity decreased, indicative of internalization of the 5G9 antigen (i.e., antigenic modulation). Upon binding of mAb 5G9 with the cell surface antigen, referred to herein as "5G9", the data evidences that the conjugate is internalized. As can be seen in FIG. 3, there is a significant decrease in the percentage of 5G9 positive cells from 80% to 20% over a two hour period (DCs cultured with GM-CSF, IL-4 and TNF- at 37° C.) and from 85% to 50% over a two hour period (DCs cultured with GM-CSF and IL-4 at 37° C.), indicating internalization of mAb 5G9 following binding with the 5G9 ligand. These data support the position that the 5G9 cell surface antigen is an antigen receptor on human dendritic cells and/or dendritic like cells.

Figure 4:
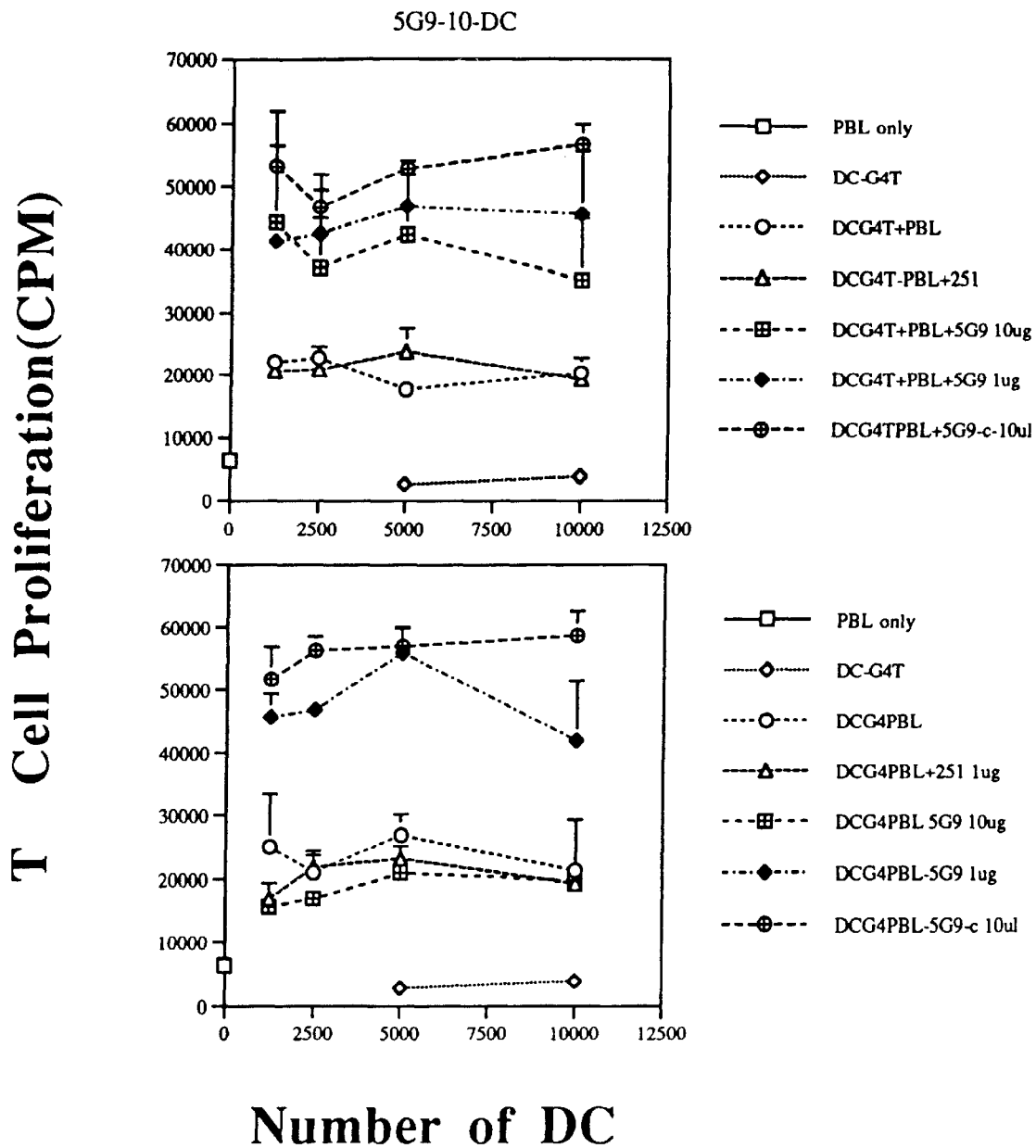
FIG. 4 comprises graphs illustrating T cell proliferation (via allogeneic mixed lymphocyte reactions) in the presence of mAb 5G9. Stimulator: D39 DCs; Responder: D40 PBL; DCG4T: DC culture includes GM-CSF, IL-4 and TNF-; DCG4: DC culture includes GM-CSF and IL-4.
Figure 5:
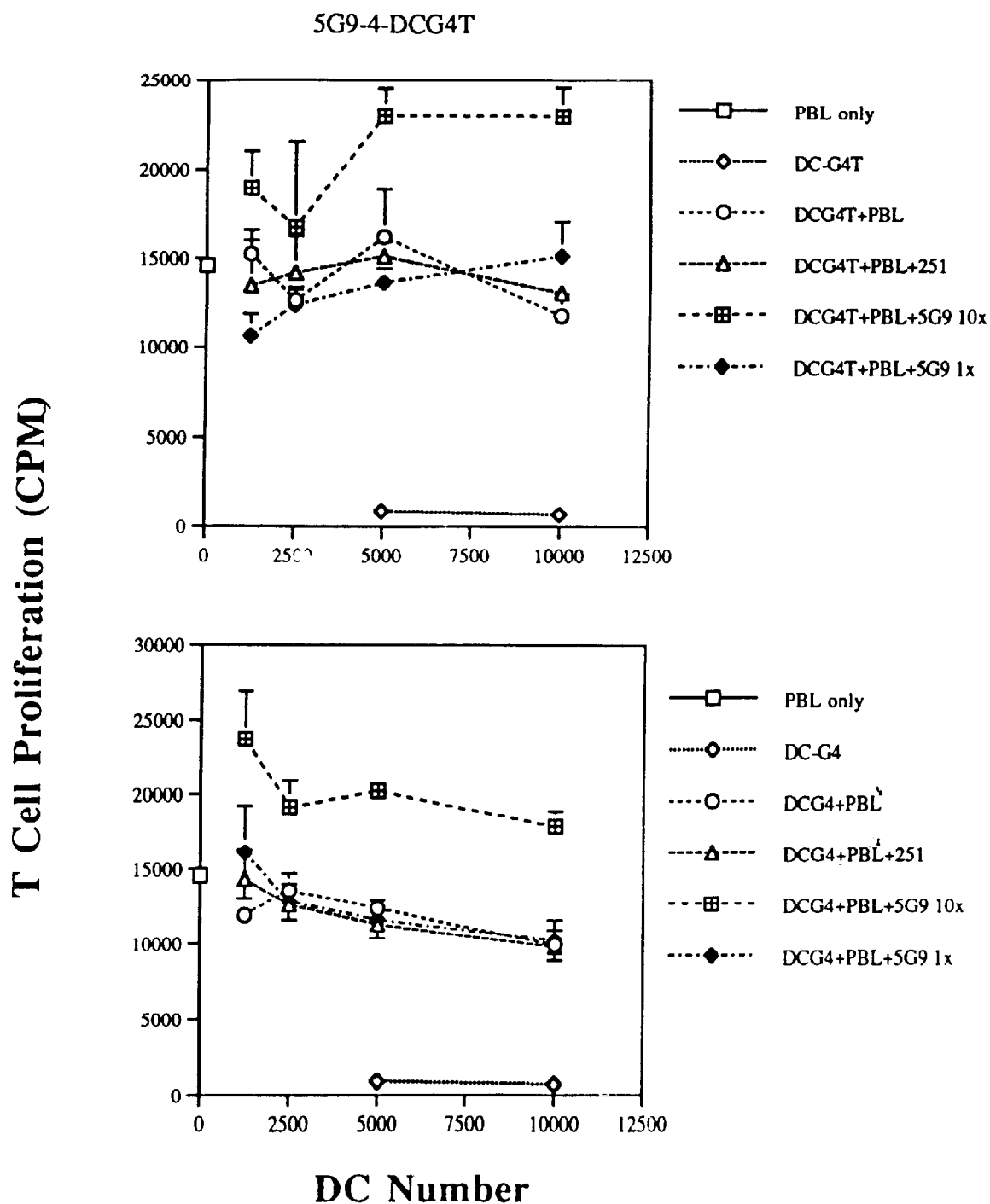
FIG. 5 comprises graphs illustrating enhancement T cell proliferation (via autologous mixed lymphocyte reaction) in the presence of mAb 5G9. Stimulator: D33 DCs; Responder: D40 PBL; DCG4T and DCG4 as defined in FIG. 5A and FIG. 5B.

An important utility for mAb 5G9 includes isolation of cells having a dendritic morphology. Such isolation provides opportunities to derive detailed characterization (including, but not limited to, nucleic acid and amino acid sequence information) regarding the 5G9 antigen; and therapeutic opportunities using cells isolated thereby. Thus, for example, by isolating quantities of cells using immobilized mAb 5G9, the ability to further investigate the 5G9 antigen is enhanced, ultimately providing the opportunity to purif both the dendritic like cells and the antigen/epitope itself. Isolation of dendritic like cells provides important therapeutic opportunities. For example, isolated dendritic like cells can be cultured and expanded, antigens of therapeutic importance can be presented to these dendritic like cells, and these "charged" dendritic like cells can thereafter be reintroduced into the patient, whereby upon such reintroduction, T cell mediated resistance to such antigen(s) can be effectuated. FIG. 4 shows graphs illustrative of the fact that T-cell proliferation is significantly enhanced in the presence of mAb 5G9. Similarly, FIG. 5 illustrates proliferation via D33 DCs.

As a research "tool", mAb 5G9 provides equivalent opportunities. For example, while the immunological importance of dendritic cells is appreciated by those in the art, i.e., the role dendritic like cells play as an adjuvant for T cell mediated immune responses, a complete understanding of the functional operation of dendritic like cells (i.e., dendritic cells) has not yet been fully elucidated. This is particularly true with respect to the role DCs play in antigen presentation. Thus, because mAb 5G9 is specific for dendritic like cells, isolation of such dendritic like cells is possible; such isolation, followed by purification thereof (using techniques known to those in the art), provides the opportunity for experimental manipulation of the isolated DCs, geared towards, e.g., more definitive understanding of the functional role of DCs.

One embodiment of the present invention provides for methods of enriching and/or purifyng dendritic like cells from peripheral blood or other physiological sources of these cells. The biologic activity of these cells may allow for their uses in settings where absolute purity is not achieved. Although, as a source, the blood is preferred, the cells of the invention may be isolated from any tissue where they reside or from which they may mature, including but not limited to the bone marrow, fetal liver, or embryonic yolk sac.

In accordance with this aspect of the invention, dendritic like cells may be isolated by separation based on the presence or absence of specific cell surface markers. It is preferable that at least one of the cell surface markers is a 220 kDa protein (antigen) as described more fully herein. The isolation techniques of the present invention may include flow cytometry using a fluorescence activated cell sorter or biotin-avidin or biotin-streptavidin separations using biotin-conjugated to marker-specific polyclonal or monoclonal antibodies and avidin or streptavidin bound to a solid support such as affinity column matrix or plastic surfaces, magnetic separations using antibody-coated magnetic beads, destructive separations such as antibody plus complement or antibody coupled to cytotoxins or radioactive isotopes for the removal of undesirable cell populations.

Alternatively, the dendritic cells may be isolated by procedures involving repetitive density gradient centrifugation, lectin chromatography, affinity chromatography involving positive selection, negative selection, or a combination thereof. Affinity chromatography with antibodies (e.g., mAb 5G9) directed to the 220 kDa surface protein may also be used. For example, most mononuclear cells may be depleted first from the blood after density gradient centrifugation and plastic adhesion, then an antibody to vimentin antigen can be used to positively select for cells. These cells may then be exposed to mAb 5G9 or subclones thereof to isolate cells expressing 5G9. A monoclonal antibody like mAb 5G9 is preferably used for recognition of the cell surface 5G9 protein. The monoclonal antibodies may be used alone or in combination with antibodies to any T cell, B cell, monocyte, natural killer (NK) cell, dendritic cell and granulocyte markers. The antibodies may be applied in any combination repeatedly or in a sequential manner for the enrichment of particular cells. Upon binding to the antibodies, the cells may be removed by adsorption to a solid surface coated with an anti-mouse antibody column, as the majority of monoclonal antibodies directed at cell surface markers are of mouse origin, or if the antibodies are conjugated with biotin, the antibody-bound cells can be removed by an avidin-coated surface; or if the antibodies are conjugated to magnetic beads, the cells expressing antigens recognized by the antibodies can be removed in a magnetic field.

While mAb 5G9 is of murine origin, other antibodies, e.g., chimeric antibodies, antibodies produced by so-called recombinant DNA techniques, and polyclonal antibodies, etc. are included within the purview of the disclosure. The specificity of such antibodies must be substantially the same, more preferably, substantially identical, for the 5G9 antigen as that elicited by mAb 5G9.

Hybridomas may be created in accordance with the protocol set forth in *Current Protocols in Immunology,* Coligan, J. E. et al. "Production of Monoclonal Antibodies" ("Coligan") which is incorporated herein by reference thereto, 2.5.1–2.5.17. Purification may be conducted in accordance with Coligan (2.7.1–2.7.12) using Protein A, Sepharose 4B columns (Pharmacia LKB Biotechnology AB, Uppsala Sweden). Antibody was determined to be murine IgG1 using Mab Check™ kit (Sterogene Bioseparations Inc., Arcadia, Calif.) following manufacturer instructions. Both the hybridoma and monoclonal antibodies produced thereby were referred to as "mAb 5G9."

The specific hybridoma and murine monoclonal antibody were generated by fusing murine myeloma cells with Balb/c mouse spleen lymphocytes immunized with Daudi cells (Burkitt lymphoma containing E-B virus genome, lacking HLA-A, B and C). Daudi cells were obtained from the ATCC. Female Balb/c mice, seven weeks old (Charles River Laboratories, Wilmington, Mass.) were utilized. Daudi cells were washed in RPMI-1640 (GIBCO BRL, Life Technologies, Inc., Grant Island, N.Y.) (FCS free), incubated at 37° C. for 2 hrs., then washed 2× in PBS. 1×10$^6$ cells were injected intraperitonealy.

Hybridomas capable of expressing mAb 5G9 were deposited with the ATCC, 10801 University Boulevard, Manassas, Va. 20110-2209(USA), on Nov. 14, 1997 under the provisions of the Budapest Treaty. The cells were determined to be viable by the ATCC on Nov. 18, 1997. The A.T.C.C. designation for the cell line 5G9 is HB12430.

In the antibody purification hybridoma cells were injected intraperitoneally into Balb/c mice. Ascites was collected and centrifuged at 8000×g for 15 minutes. Supernatant was removed and filtered through a 0.45, µm filter. The protein was precipitated by adding a saturated ammonium sulfate solution to a final concentration of 45% saturation. The precipitate was dialyzed in PBS (pH 8.0) at 4° C. for 24 hours. Antibody was purified by a protein-A Sepharose column (Pharmacia LKB, Piscataway, N.J.) and the purity determined by sodium dodecyl sulfate polyacrylamide gel electrophoresis (SDS-PAGE).

Blood dendritic cells were enriched following the procedure set forth in Steinman, R. M. et al. 87 PNAS 7698 (1990) (hereinafter "Steinman") which is hereby incorporated by reference thereto in its entirety. Monocyte dendritic cells were generated by culturing adherent monocytes in RPMI-1640, 10% FCS (GIBCO BRL), with 50 µg/ml GM-CSF, 1000 U/ml IL-4 and 10 µg/ml TNF-α (all from GIBCO) (referred to herein as "G4T") or 50 µg/ml GM-CSF, and 1000 U/ml IL-4 (referred to herein as "G4"). Paraffin and frozen tissue sections of human tonsils were utilized; human tonsil samples were obtained from the University of Pittsburgh.

Erythrocytes and platelets were removed from leukocyte-enriched leukopaks (obtained from Central Blood Bank, Pittsburgh, Pa.) with lysing buffer, and washed 210×g 4 times with PBS. Mononuclear cells were cultured overnight in RPMI-1640 medium containing 10% heat-inactivated FCS, 10 mM glutamine, and penicillin/streptomycin. A DC-enriched population of cells was obtained as previously described with some modifications. Briefly, the mononuclear cells were suspended in IMDM (GIBCO BRL) medium containing 0.2% BSA (SIGMA, St. Louis, Mo.) in 1×10$^7$/ml were cultured with 2–3 subsequent 45 min periods at 37° C. in 150×15 mm petri dishes (Becton Dickinson Labware, Lincoln Park, N.J.) to remove monocytes. Monocyte-derived dendritic cells were obtained by culture of the adherent monocytes in RPMI-1640 complete medium containing 1000U/ml IL-4, 100 ng/ml GM-CSF and 10 ng/ml TNF-α. The remaining nonadherent cells were resuspended at 2×10$^7$ cells/ml in RPMI-1640 containing 1% FCS and incubated with mAb OKT-3 for 30 min at 4° C., and washed 3× and incubated with sheep anti-mouse IgG Dynabeads M-450 (Dynal A. S, N-0212 Oslo, Norway) for 30 min at 40° C. The cell suspension was washed 3× against Dynal MPC (Dynal A. S, N-0212 Oslo, Norway) to remove T cells. The T cells and monocyte-depleted mononuclear cells were resuspended at 5×10$^6$/ml and layered onto hypertonic 14.5% metrizamide (SIGMA, St. Louis, Mo.) in 15 ml conical centrifuge tubes and sedimented at 650×g for 15 min at room temperature. DC-enriched cell populations were harvested from the interface of the metrizamide gradient.

To isolate 5G9 positive population of cells, monocytes were depleted from mononuclear cells by 2–3 rounds of adherence to Petri dishes. Non-adherent cells were either immediately or after culturing 1–5 days in RPMI-1640 complete medium with 1000 u/ml IL-4, resuspended in 5G9 culture supernatant in concentration of 2–4×10$^7$/ml, incubated for 30 min at 4° C., washed 3×, resuspended in RPMI-1640, 2% FCS and mixed with sheep anti-mouse IgG Dynabeads M-450 with continuous mixing for 60 min at 4° C. (cell number/beads=100/1). 5G9 positive cells were obtained by washing the cell suspension 3× against Dynal MPC. The cells attached to magnetic beads were suspended in RPMI-1640 10% FCS and incubated at 37° C. overnight. About 30–50% of isolated 5G9$^+$ cells were detached from the Dynabeads and washed three times against Dynal MPC.

Cell lines analyzed herein are listed in Table 1. Cell lines were cultured in RPMI 1640 (GIBCO, Grand Island, N.Y.) containing 10% FBS (Hazelton Dutchland, Inc., Denver, Pa.) in an humidified atmosphere of 5% $CO_2$ and air. Cells in log phase were freshly harvested from culture, washed three times and resuspended in RPMI 1640 medium before use.

TABLE 1

Reactivity of mAb 5G9 with cell lines

| Cell Type | Cell Line | % Positive |
| --- | --- | --- |
| Lymphoma | Daudi | 98 |
|  | Raji | 70 |
|  | DB | 70 |
|  | SUDHL-4 | 95 |
|  | L428 | — |
| ALL | Molt | — |
|  | CEM | — |
|  | Jurkatt (T) | — |
| AML | HL60 |  |
|  | NB4 |  |
|  | KG1a |  |
|  | K562 |  |
|  | U937 |  |
| Myeloma | RPMI 8226 | 90 |
| CLL |  | 89.8 ± 2.7* |

Negative reaction is defined as <2% of positive cells.
*n = 3

The specificity mAb of the present invention for cell lines (e.g., chronic lymphocytic leukemia cell over ALL and AML) shown in Table 1 suggest potential uses of mAb 5G9 or other mAb specific for the 220 kDa 5G9 protein. Thus, the mAb of the present invention may be utilized in a number of ways. Numerous bioactive agents may be conjugated to the mAb in accordance with the present invention including drugs, toxins or toxin fragments, growth modifying biological response modifiers, enzymes, liposomes, radioisotopes, photodynamic agents, or other antibodies including anti-idiotype antibodies, chimeric antibodies and monoclonal antibodies or fragments of such antibodies. In addition, the mAb or fractions of these mAbs may be incorporated into other matrices for use in separation schemes which are based upon antibody-antigen reactions. Numerous drugs may be complexed with the antibody of the present invention. In general, when such drugs are used for detecting or treating leukemia or lymphoma cells, such drugs are cytotoxic agents such as methotrexate. The antibody of the present invention may similarly be complexed with toxins, desirably those which are especially effective against cancer cells, by methods well known to those skilled in the art. The antibody of the present invention may be complexed with growth modifying biological response modifiers, especially those which suppress cell growth when the complex is to be used in cancer treatment. Such biological response modifiers may be broadly considered to have hormone-like activity and as such may be broadly classified as hormones. Suitable biological response modifiers or hormones for forming such complexes with antibodies are known to those skilled in the art and for example include interleukins, interferons, growth factors, and lymphokines. Such complexes have utility in cancer management as aids for both cell targeting and growth control. Complexes may be formed between the antibody of the present invention and radioactive agents. Methods for forming complexes between antibodies and radioactive agents are well known and an example of such a method is subsequently described herein. Complexes may also be formed between enzymes and the antibody of the invention. The antibodies of the present invention may also be complexed with photodynamic agents.

The antibody of the present invention may be complexed with other antibodies or fragments to increase targeting ability (bispecific antibodies) or to utilize the additional antibody to achieve a desired cancer cell response, e.g., to more efficiently bring cytotoxic T cells to tumor cells. Methods for forming complexes between antibodies are well known in the art.

Phycoerythrin-labeled mouse anti-human mAbs CD3, CD4, CD5, CD10, CD11b, CD13, CD14, CD19, CD20, CD21, CD22, CD33, CD38, CD40, CD56 HLA-Dr were purchased from Becton Dickinson. CD83 was purchased from Immunotech. Indirect immunofluorescence staining was conducted after washing the cells 2× with PBS containing 1% BSA and 0.1% sodium azide. Cells were incubated with mAb 5G9 for 30 min at 4° C., washed 2× and incubated with FITC labeled goat F(ab')2 anti-mouse IgG (H+L) (CALTAG Laboratories, Burlingame, Calif.) and washed prior to analysis on FACScan system (Becton Dickinson Immunocytometry System). Double staining involved labeling with mAb and goat F(ab')$_2$ anti-mouse IgG followed by incubation 10 min with 10% mouse serum at 4° C. prior to adding a phycoerythrin-conjugated mAb.

The cytospin slides of peripheral blood, cultured moDC, purified 5G9$^+$ cells were stained with Wright-Giemsa by Ames HEMA-TEK Slide stainer (Curtis Matheson Scientific, Inc., Houston, Tex.). Tissue was fixed in 10% neutral buffered formalin, embedded in paraffin, and 4 micron sections were cut and stained with hematoxylin-eosin (H-E) for microscopic examination.

For cell sorting, monocyte- and T cell-depleted mononuclear cells were suspended in 5G9 culture supernatant in concentration of $5 \times 10^6$/ml and incubated for 30 min at 4° C., then washed and incubated with goat anti-mouse IgG-FITC. The cells were washed 3× and sorted on a FACStar Plus (Becton Dikinson). Large (high light scatter) 5G9 positive cells were selected as Dendritic like B cells.

In the Mixed Leukocyte Reaction (MLR), stimulators for the MLR were total PBL, 5G9$^+$ cells, 5G9$^-$ cells, 5G9$^-$ B cells, and monocytes derived from the separation procedures, cultured in IL-4/GM-CSF or M-CSF. 5G9$^-$ B cells were obtained by negative selection of 5G9$^-$ PBL population with a cocktail of mAbs CD3, 3G8 (CD16), 251 (CD33) and sheep anti-mouse IgG Dynabeads M-450. These cells were irradiated 3000 rads and added in graded doses to $2 \times 10^5$ allogeneic or syngeneic mononuclear cells in 96 well U-bottom tissue culture plates in final volume of 0.2 ml. The medium used for MLR was AIM-V medium (GIBCO BRL) containing 10% inactivated human AB serum. Proliferation was measured by the uptake of [$^3$H]thymidine (1 μci/well) added 8 hr before the end of culture (37° C., 5% CO2) on the 5th day, counted in 1205 Betaplate counter (Wallac Inc. Gaithersburg, Md.)

Vectastain ABC kit (Vector Laboratories, CA94010) was used for immunohistochemical analysis (peroxidase-AEC) of 5G9, CD19 or CD21 expression on cytospin slides for PBL, DC, MoDC, 5G9+ cells or tissue section slides, following the manufacturer's instructions.

For scanning electron microscopy, cytospin glass discs were fixed in 1% glutaraldehyde and dehydrated in a concentration gradient of ethanol. Cells were then critical-point dried through $CO_2$ to maintain cellular ultrastructure and attached to carbon planchettes with colloidal graphite, coated with a 250 A layer of gold in a sputter-coater, and studied in a scanning electron microscope.

The evidence presented herein supports the position that mAb 5G9 reacts with cells having a dendritic like morphology specifically binding with a cell surface antigen, referred to herein as "5G9". As further evidenced by the following examples, binding of mAb 5G9 with 5G9 led to internalization of the mAb 5G9-5G9 complex, supporting the position that at least one function of the 5G9 cell surface antigen is a DC antigen receptor.

As is shown in a two-color flow cytometry, protocol was utilized to investigate binding of mAb 5G9 to monocytes. MAb 5G9 reacted with 40–60% of peripheral blood CD19$^+$, HLA-Dr$^+$B cells, and these cells were CD3 negative, CD56 negative and CD14 negative.

Some of the reagents used herein are defined herein below. "IFA Medium" consisted of 33 ml 30× Dulbecco's PBS-A (excluding calcium and magnesium); 20 ml 5% sodium azide (0.1% final); about 700 ml glass distilled (deionized) water, pH adjusted to 7.2 to 7.4 with 1 M HCl or NaOH (as needed); 40 ml Clarified Newborn Serum (which is preferred) or Fetal Calf Serum (4% final); and glass distilled (deionized) water QS to 1L. "IFA Medium with Blockers" consisted of 480 ml IFA Medium; 10 ml Clarified Human AB Serum (2% final); and 10 ml Clarified Goat or Sheep Serum (2% final). "IFA Medium with Super Blockers" consisted of 100 ml IFA Medium with Blockers; and 1 ml normal mouse serum or ascites fluid. "Lysing Agent" consisted of 4.15 g ammonium chloride (0.83% final); 0.5 g potassium bicarbonate; 1.0 ml 5% sodium azide (0.01% final); 0.15 g disodium EDTA; about 400 ml glass distilled (deionized) water; pH adjusted to 7.2 to 7.4; and glass distilled (deionized) water QS to 500 ml. "Fixative" consisted of 3.3 ml 30× PBS-A; about 60 ml glass distilled (deionized) water; pH adjusted to 7.2 to 7.4; 20 ml 10% methanol free formaldehyde (2% final; Polyscience Inc., Warrington Pa., Cat. #4018); and glass distilled (deionized) water QS to 100 ml.

In the Clarifying Sera Method, serum was heat inactivated in 56° C. water bath for 30 min; followed by centrifugation in SORVAL™ medium speed centrifuge (55-34 rotor) with approximately 40 ml polycarbonate tubes, 15,000 RPM for 30 min (about 25,000×g); followed by removal of lipid material (if any) from surface with Pasteur pipette; followed by decant of clarified serum.

In the Staining Methods used throughout this disclosure, the medium was chilled and kept cold. Ficoll/hypaque separated cells (300×g, about 1300 RPM, 7 min) were washed 1× in IFA Medium. RBCs were lysed (if necessary) by resuspension in Lysing Agent (10 ml), followed by incubation in 37° C. water bath for 10 min. Cells were pelleted, and the Lysing Agent was poured off.

Cells were washed with IFA Medium, followed by IFA Medium with Blockers; cells were then counted, followed by resuspension at $5 \times 10^5$ cells/ml in IFA Medium with Blockers. 1 ml ($5 \times 10^5$ cells) was then added to "snap-cap"

tube, pelleted, and decanted. MAb 5G9 was added, followed by 30 min. incubation on ice. This was followed by washing with IFA Medium (300×g, 7 min) and one wash with IFA Medium with Blockers; the medium was then poured off.

FITC conjugated goat anti-mouse IgG (Sigma, F2883), 50 μL diluted 1/100 in IFA Medium with Blockers, was then added to the tubes, followed by incubation for 30 min, in the dark, on ice. Following a wash with IFA Medium with Blockers and IFA Medium with Super Blockers, the medium was poured off. PE conjugated monoclonal antibody (20 μL) was added to tubes (prior thereto, antibody was Eppendorf centrifuged at 10,000 RPM for 10 min). This was followed by incubation for 30 min, in the dark, on ice. This was followed by IFA Medium wash 2×, with medium poured-off. 50 μL Fixative was added per tube. Following a minimum of 30 min/maximum of 12 hrs, 150 μL PBS-A was added per tube. Tubes were capable of being stored (wrapped in foil) in the dark for no more than one week prior to analysis.

Results of the binding of mAb 5G9 with monocyte derived dendritic cells over time are presented in FIG. 3 (as indicated, conditions included with or without the sodium azide).

FIG. 3 illustrates the binding of mAb 5G9 with monocyte derived dendritic cells. DCs or MoDCs ($2 \times 10^5$ cells in 100 μl RPMI-1640, 1% FCS, with or without 0.1% sodium azide) were incubated in 12×75 FALCON™ plastic tubes, with a final concentration of 200 μg/ml mAb 5G9, at 4° C. for 30 min. Cell suspension was then washed with this medium, with or without sodium azide. Following incubations (as indicated) at 4° C. or 37° C., cells were stained with FITC labeled goat F(ab)2 anti-mouse IgG (H+L) (Caltec Laboratories). Following 30 min incubation, cells were washed 2× with PBS, 1% BSA, 0.1% sodium azide, fixed with 2% paraformaldehyde, followed by flow cytometry analysis, as above.

FIG. 4 which illustrates T cell proliferation (via allogeneic mixed lymphocytes) indicates MoDCs, generated by culturing adherent monocytes in RPMI-1640 medium, and blood DCs, were enriched using the procedure of Steinman, followed by culturing in 6 well culture plates in RPMI-1640, 10% FCS with 50 ng/ml GM-CSF, 1000 U/ml IL-4 and 10 μg/TNF-α, or 50 μg/ml GM-CSF, 1000 U/ml IL-4. At 5, 8 and 12 days, cells were taken out from the cultures and irradiated (3000 rads) as stimulator cells. It should be noted that FIG. 4 was generated using supernatant, therefore, while it is shown below that cells expressing the 5G9 protein result in T cell proliferation, it may be possible that "dirty" supernatent is showing the effect.

MLR was conducted using 96 well flat bottom plates, with RPMI-1640, 10% FCS as culture medium. $2 \times 10^5$ autologous cells (frozen and dissolved), or allogeneic PBL cells (monocytes removed by adherent separation), were added to each well in a final volume of 200 μl as responder cells. Following a 5 day incubation in 37° C., 5% $CO_2$, 1 μci $^3$H-TdR was added to each well. Cells were harvested after 8 hr and counted in 1205 Betaplate counter (Wallac Inc., Gaithersburg Md.). The results are shown in FIG. 5. These graphs illustrate significant enhancement of T cell proliferation in the presence of mAb 5G9.

Figure 6:
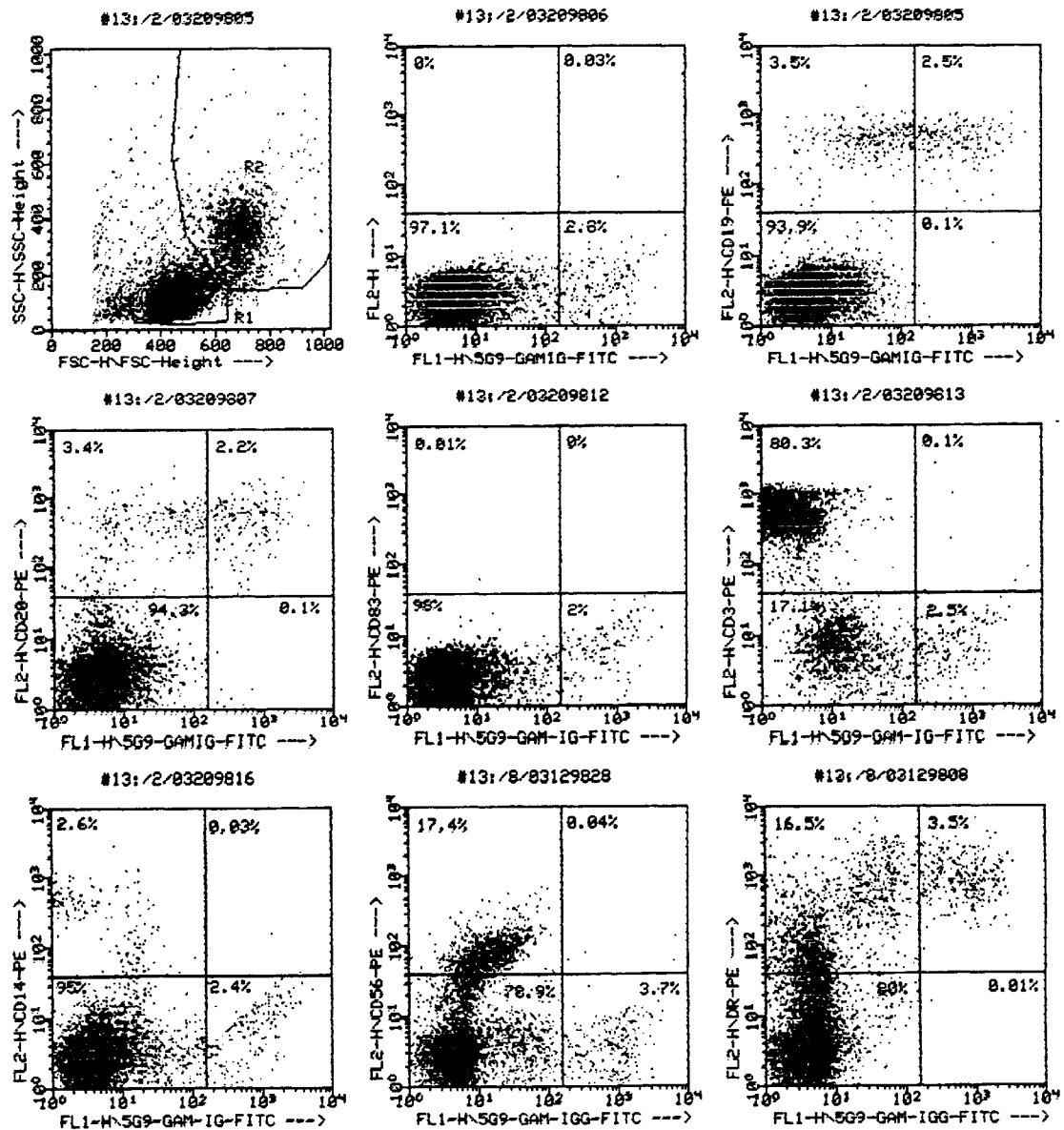
FIG. 6 illustrates the reaction of mAb 5G9 to peripheral blood mononuclear cells as assessed by two-color flow cytometry analysis.
Figure 7:
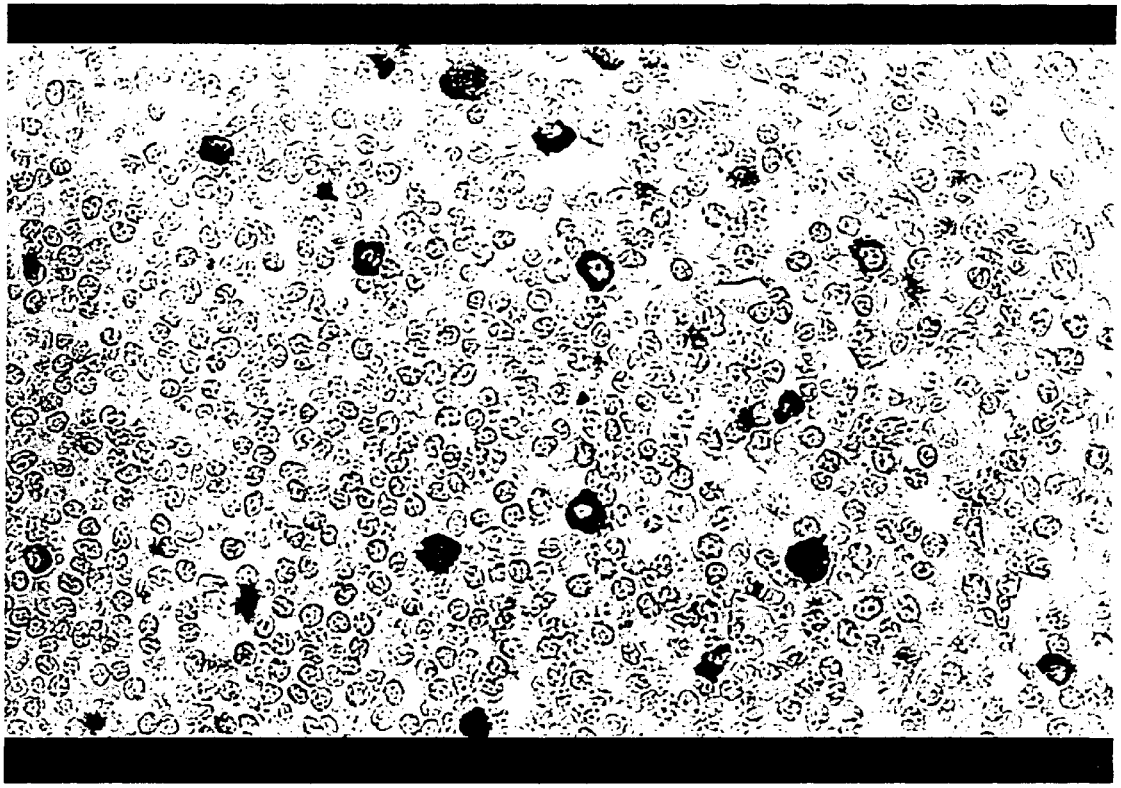
FIG. 7 illustrates an immunohistochemical study (peroxidase-AEC) of human tonsil sections with mAb 5G9.
Figure 8:
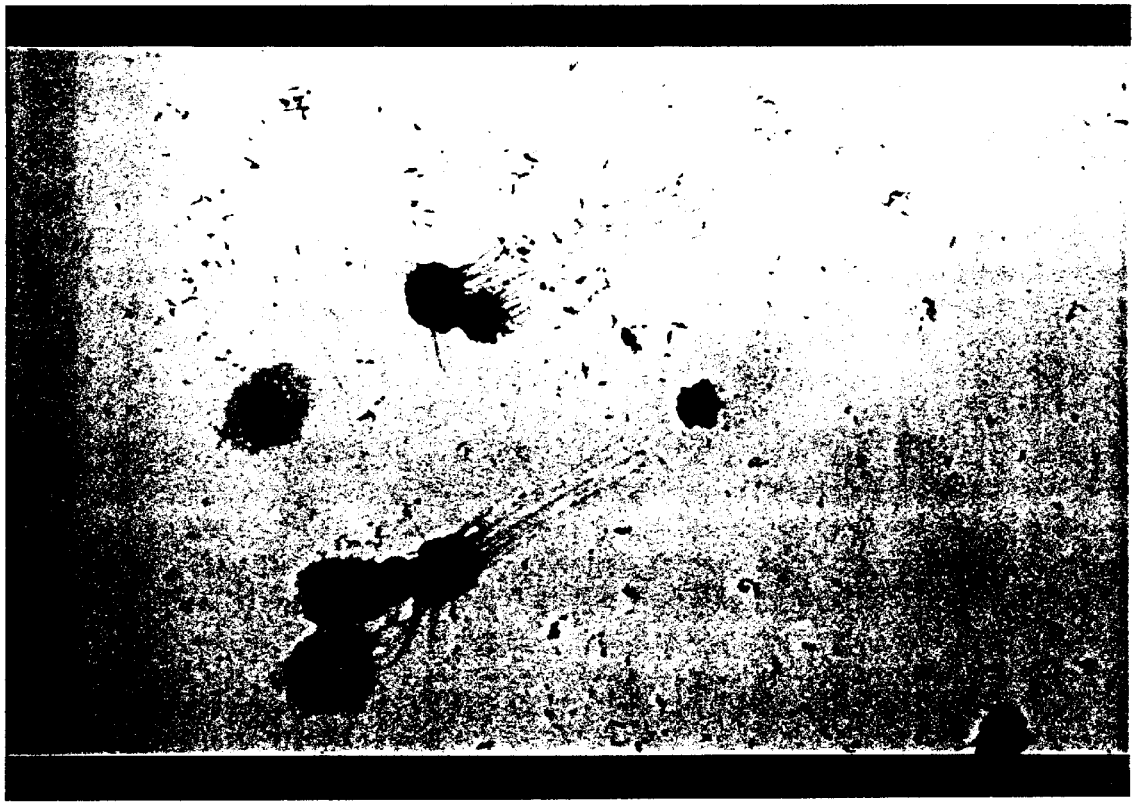
FIG. 8 illustrates an immunohistochemical study (peroxidase-AEC) of monocyte-derived dendritic cells (MoDC) with mAb 5G9.

As shown in FIG. 6, mAb 5G9 reacted with 40–60% peripheral blood high HLA-DR expressing B cells. MAb 5G9 did not react with peripheral blood erythrocytes, granulocytes, platelets (data not shown), T cells ($CD3^+$) and NK ($CD56^+$) cells, and monocytes ($CD14^+$) (n=8). Double staining $5G9^+$ cells in resting PBL with CD83 showed no double positive cells (FIG. 7). As can be seen in FIG. 7 and FIG. 8, mAb 5G9 reacted with scattered cells on human tonsil sections which appeared morphologically to be dendritic cells. This mAb reacted with lymphoma cell lines and cells from chronic lymphocytic leukemia (CLL) patients (3 of 3), but did not react with AML and ALL cell lines or AML and ALL patient-derived cells (See Table 1 above).

Immunohistochemical analysis of 5G9 antigen expression on blood DC cultured with GM-CSF/IL-4 (5 day incubation) was evaluated using VECTASTAIN ABC™ kit (Vector Laboratories, Calif.). For FIG. 8, MoDC were cultured with IL-4 1000 u/ml, GM-CSF 50 ng/ml and TNF-α (10 ng/ml) for 4–10 days. On cytospin slides of MoDC cultured with IL-4, GM-CSF and TNF-α for 4–10 days, mAb 5G9 reacted strongly with typical dendritic morphology cells with exceptional long membrane processes different from other MoDC. These cells comprised about 2.5±1.7% of MoDC cells (n=6, range 1.25–6.1%), and were double stained by mAb CD19 and CD20 by flow cytometry (data not shown).

Figure 9:
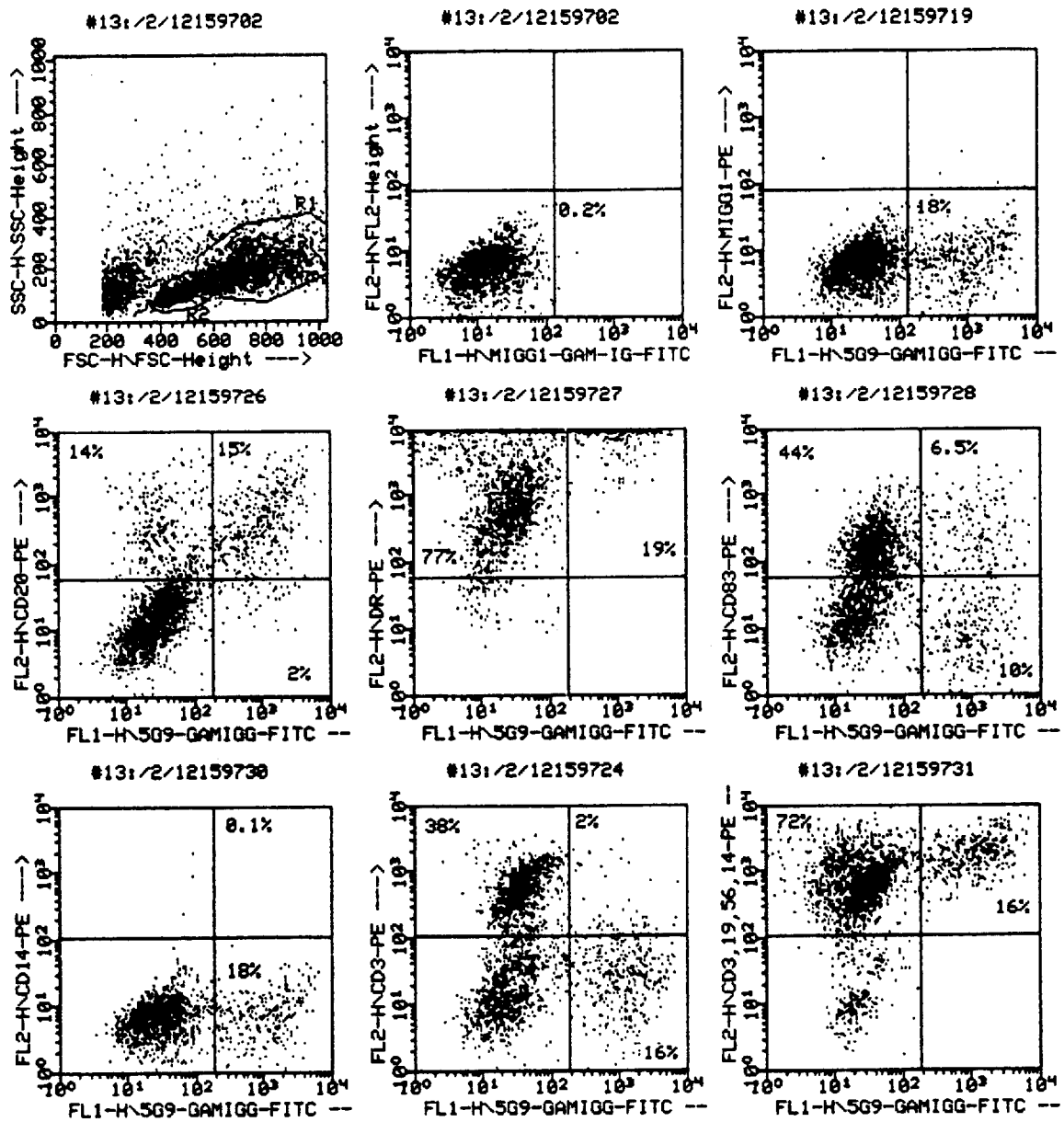
FIG. 9 illustrates the reaction of mAb 5G9 with classical dendritic cells.

Human blood mononuclear cells were enriched for DC by metrizamide density gradient centrifugation as described herein and known in the art to determine whether DC population expressed detectable levels of 5G9 antigen. MAb 5G9 reacted with a fraction of metrizamide low density mononuclear cells which represented about 17±4% (n=4) of DC enriched fraction of cells. This fraction of cells was not the lineage negative, CD83 positive dendritic cells described previously. These cells were CD19, CD20, HLA-DR positive, CD2, CD14, CD56 negative and CD83 dim (most CD83 negative) (FIG. 9).

Figure 10A:
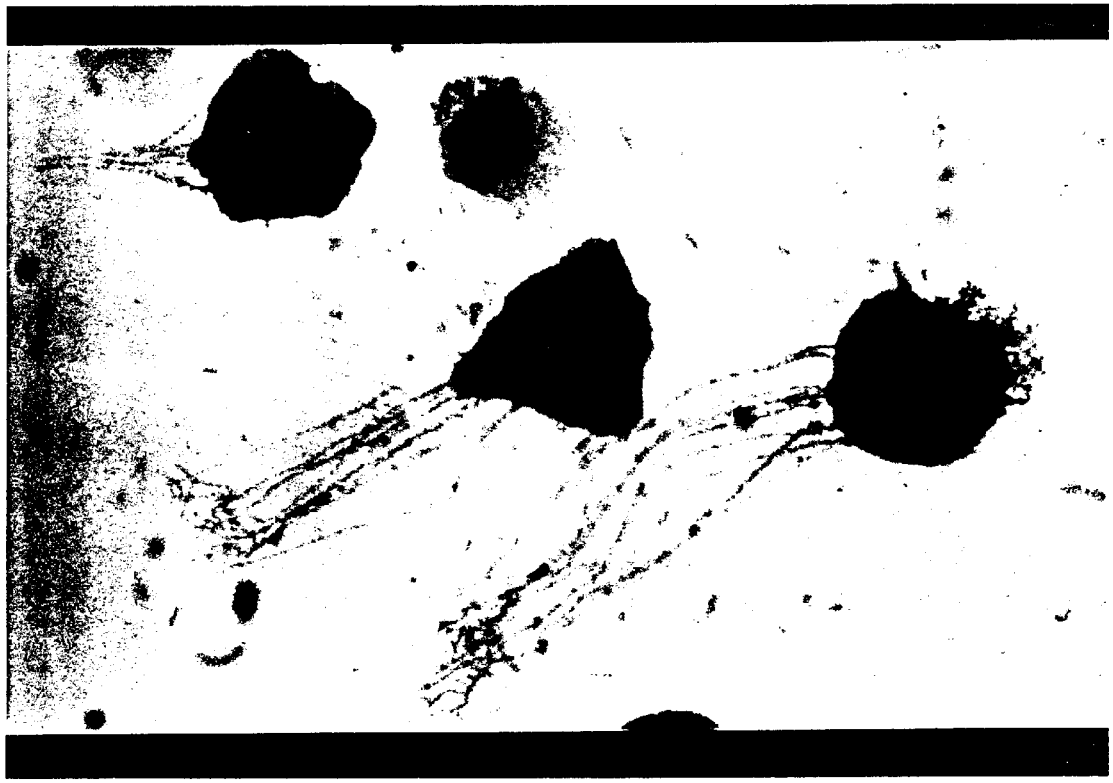
FIG. 10A illustrates 5G9 positive cells isolated by positive selection immediately after isolation with goat anti-mouse IgG magnetic beads.
Figure 10B:
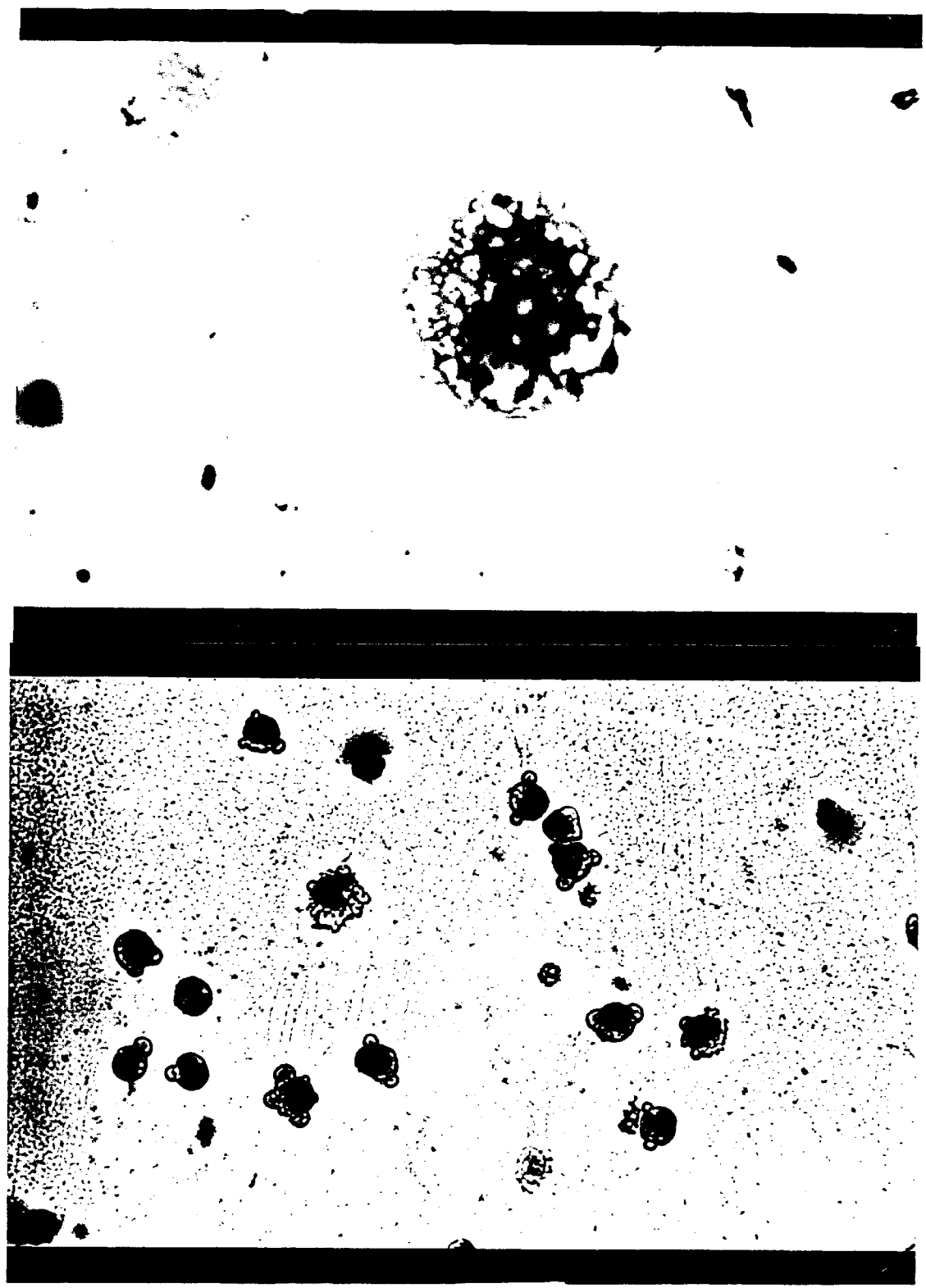
FIG. 10B illustrates Wright-Giemsa sensing of the positively selected 5G9+ cells immediately after isolation (top) and after 4 days in culture (bottom) in RPMI-1640 medium, 10% FCS and 1000 u/ml IL-4. Immediately following isolation.

5G9 positive cells were successfully isolated by positive selection with mAb 5G9 and goat anti-mouse IgG magnetic beads as described herein. Wright-Giemsa (FIGS. 11 A, B) and immunohistochemical (FIG. 12) staining of 5G9 positive cells were performed immediately after isolation by magnetic beads, one day or 4 days in culture. Immediately following isolation, 4.7±1.9% (n=7, range 2–7%) of isolated cells displayed DC morphology in Wright-Giemsa stained cytospin slides. FIG. 10 illustrates examples of dendritic like morphology isolated by the procedures discussed herein. The top slide in FIG. 10B is immediately after isolation and the bottom slide is after 4 days in culture. Some donor cells showed as much as 40–50% of Dendritic like morphology (e.g., long and thin processes) at the first day of isolation. The proportion of DC-like cells increased to 31.2±15% and 60±14.5% after 1 or 4 day culture in complete RPMI1640 medium supplemented with IL-4 (1000 u/ml). When human PBMC were cultured in IL-4 for 4 days before bead isolation, the majority of isolated cells showed DC morphology (64.5±8.6%, range 54–75%, n=4). After 4–6 days in culture most of the small lymphocytes apoptosed and died, and the percentage of Dendritic like cells increased to 50–80%. Morphological changes occurred in DC-like cells, with larger cell size and shorter processes.

Figure 11A:
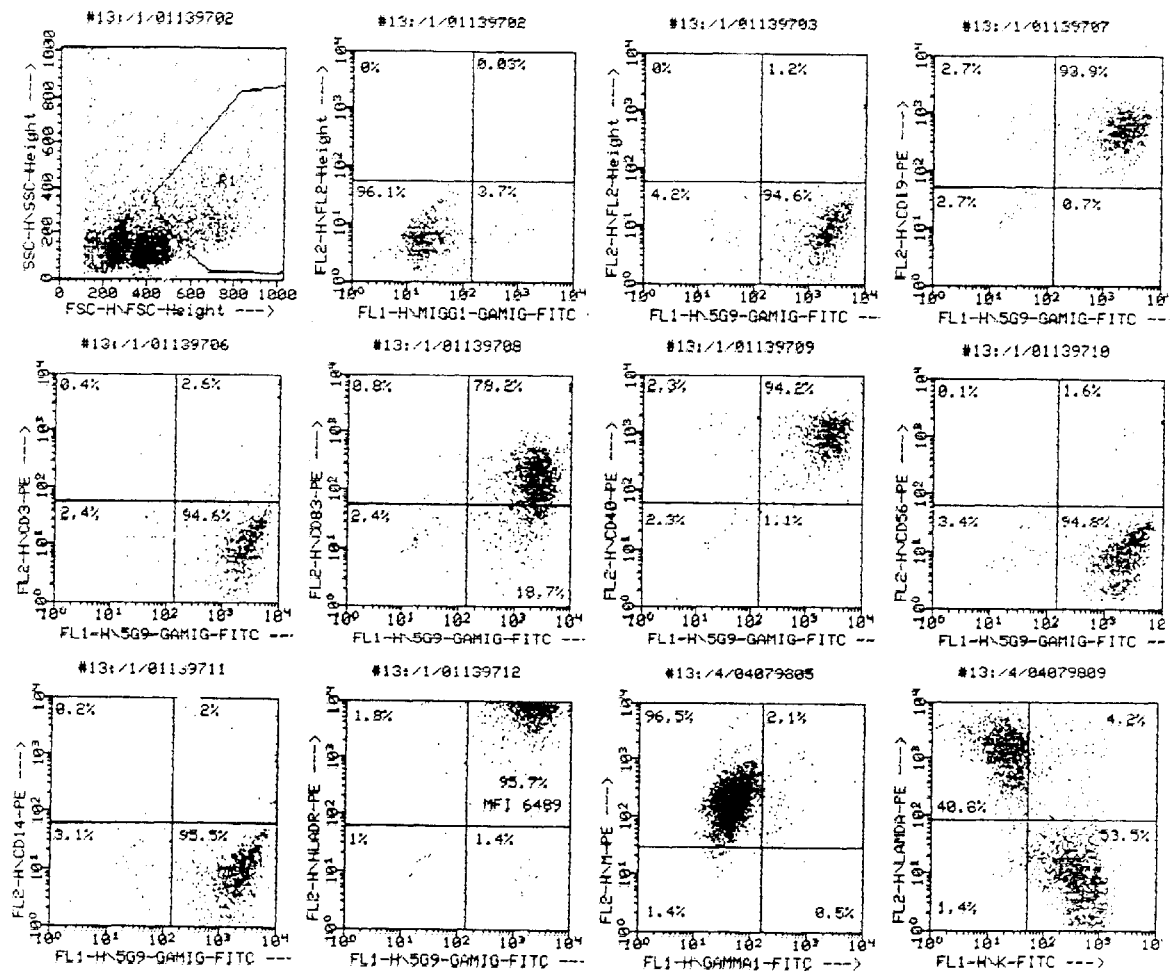
FIGS. 11A and 11B illustrate a flow cytometry analysis of magnetic bead-isolated 5G9+ cells.
Figure 11B:
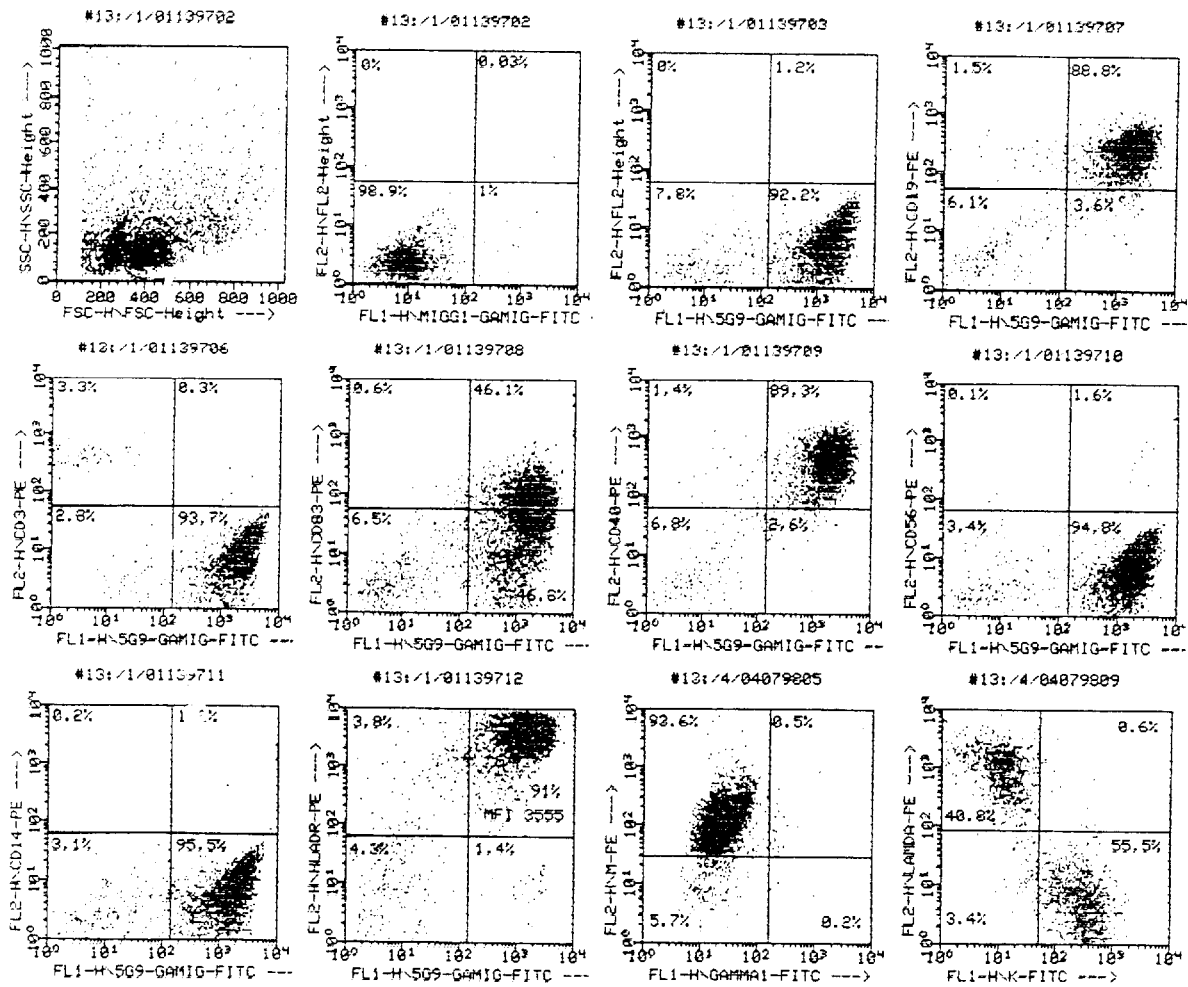
Figure 12:
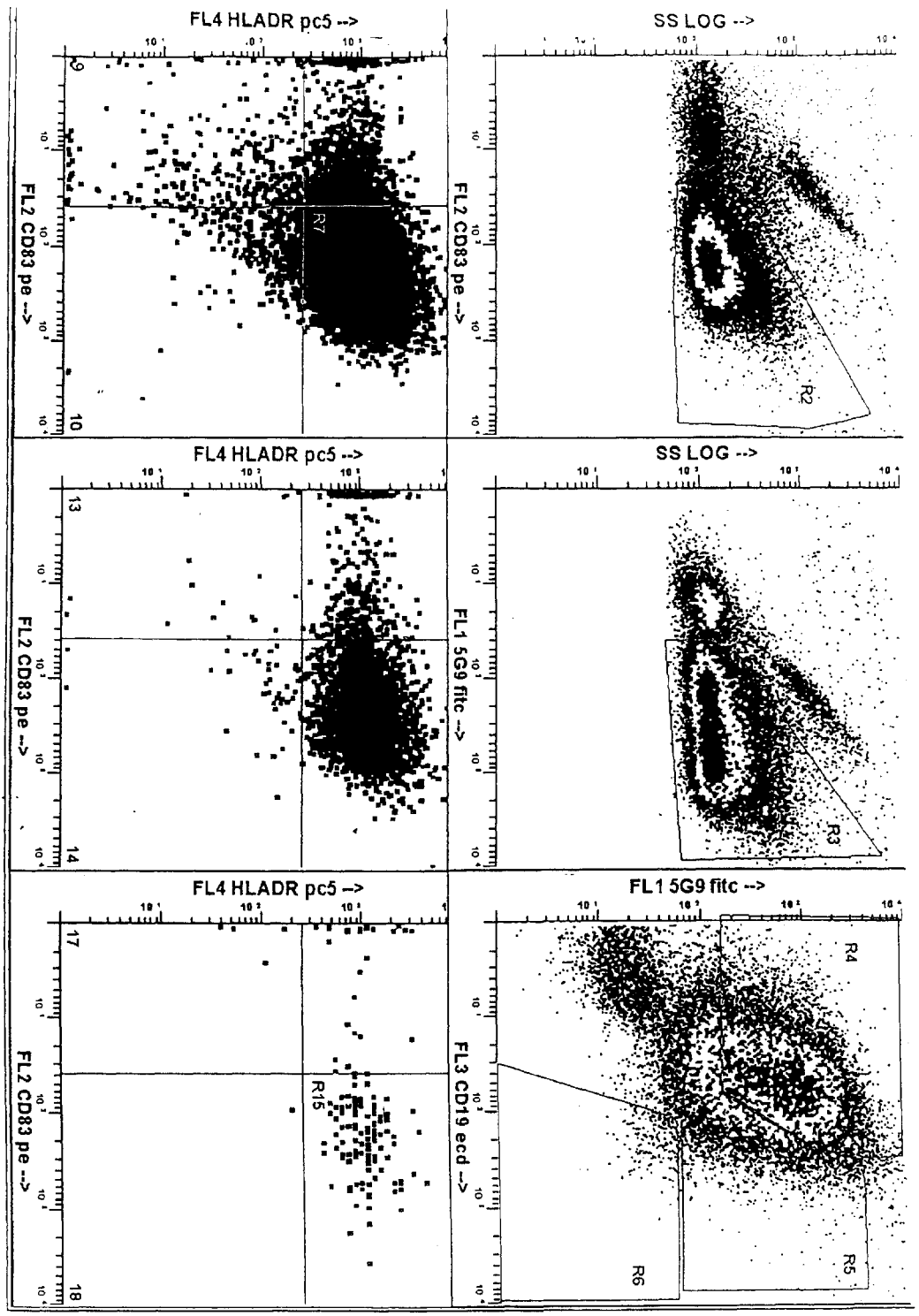
FIG. 12 illustrates a color flow cytometry analysis of mAb 5G9 and magnetic beads purified cells.

FIGS. 11A and 11B illustrate the flow cytometry analysis of magnetic beads isolated $5G9^+$ cells. A group of small cells in the low light scatter gate (FIG. 11B) and a group of larger cells in the high light scatter gate (FIG. 11A) were demonstrated on forward and side scatter. Both groups of cells showed the same phenotype (CD19, CD20, CD22, CD40, HLA-DR, CD83, immunoglobulin μ chain positive and either kappa- or lambda-light chain positive). They did not express CD3, CD4, CD5, CD10, CD13 CD14, CD16, CD33, CD56, CD64. The only substantial difference between low light scatter gated and high light scatter gated of $5G9^+$ cells was that the cells in the high light scatter gate had higher HLA-DR fluorescent intensity (3555 vs 6389) and higher percentage of $CD83^+$ cells (46.1 vs 78.2), suggesting that a higher DC composition existed in the high light scatter gate. The demonstration of DC morphology and expression of CD83 of these cells may have occurred during the separation procedure or after the binding of 5G9 to these cells. Previous studies proved that regardless of the culture period (0–72 hr) B cells did not express detectable levels of CD83 as determined by flow cytometry analysis. Therefore, the expression of CD83 on 5G9$^+$ cells after isolation by mAb 5G9 and magnetic beads (and following 24 hr culture), may have been induced by the binding of mAb 5G9 to B cells. Four color flow cytometry analysis of mAb 5G9 and magnetic beads purified cells showed that these cells expressed CD83-PE, CD19-ECD, HLA-Dr-PC5 and 5G9-FITC simultaneously (See FIG. 12).

Figure 13:
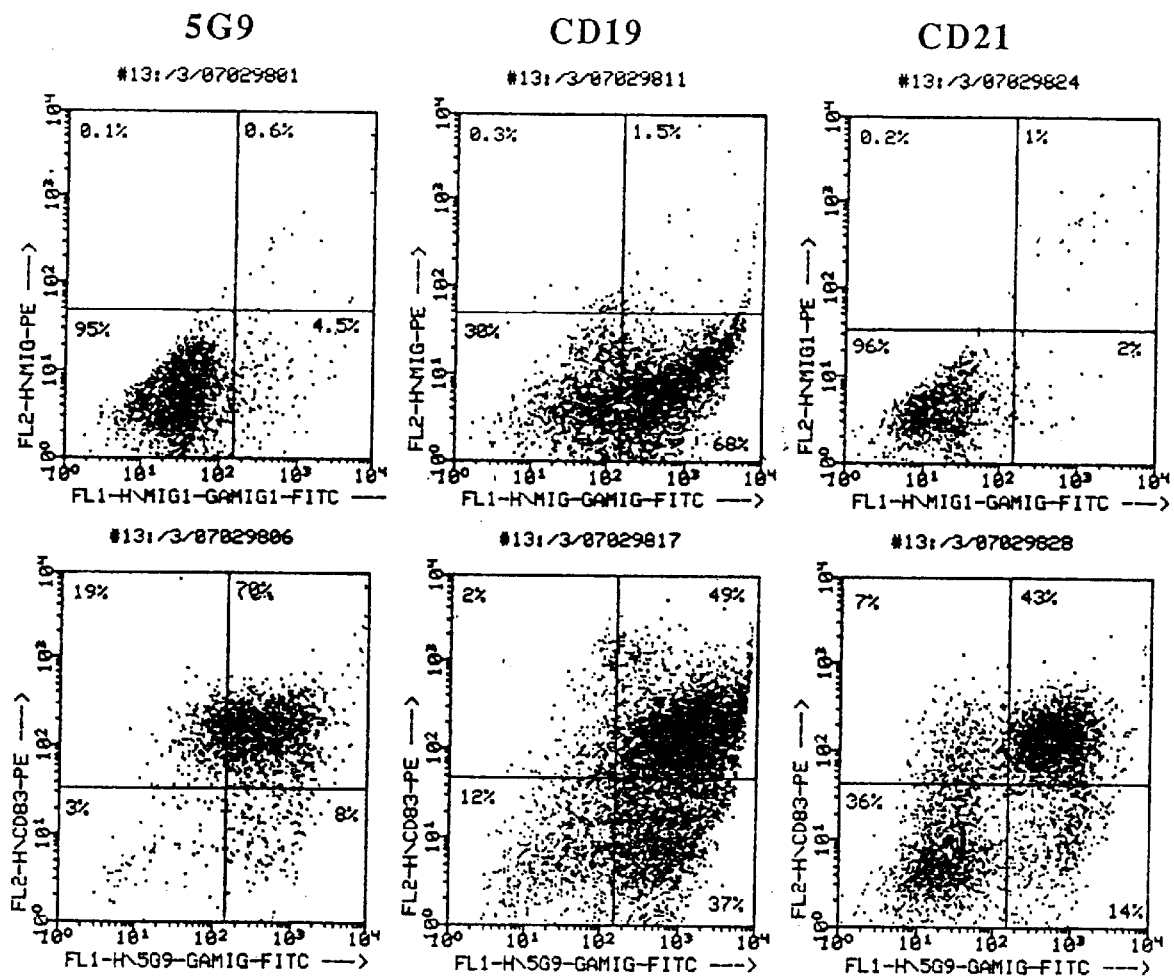
FIG. 13 illustrates CD83 expression on mAb 5G9, CD19, CD21 isolated cells.

The specificity of mAb 5G9 to DC-like B cells was compared with mAb against CD19 (B4) and CD21. The three mAb were used in the same procedure as described above to isolate B cells from same donor's PBMC after cultured in RPMI-1640, 10% FCS and 1000 U/ml IL-4 for 4 days. 5G9$^+$, CD19$^+$ or CD21$^+$ cells were isolated as described herein. Referring to FIG. 13, the left panel showed mAb 5G9 isolated cells; the middle panel showed CD19 isolated cells; the right panel showed CD21 isolated cells. The upper panel showed mouse IgG1 and goat anti-mouse IgG-FITC and mouse IgG1-PE control; the lower panel showed 5G9, goat ant-mouse IgG-FITC and CD83-PE. The results showed that there were 89% of CD83$^+$ cells in 5G9 isolated fraction and 51%, 47%, respectively, in mAb CD19 and CD21 isolated fraction. In the mAb CD21 isolated cell population, 50% of the cells were 5G9$^+$ and only 5G9$^+$ cells were double positive for CD83 (FIG. 13).

Figure 14:
FIG. 14 illustrates a scanning electron microscope study of 5G9+ cells. The Top Cells show characteristic DC morphology. The Bottom Cell shows "porcupine like" DC morphology.
Figure 14:

Under the phase contrast microscope, it was observed that DC-like 5G9$^+$ B cells cultured at 37° C. had the ability to extend and retract cell membrane processes constantly, and had marked cell motility (data not shown). The scanning electron microscope study of 5G9+ cells revealed a characteristic DC morphology and also a "porcupine like" DC morphology (See FIG. 14).

Figure 15:
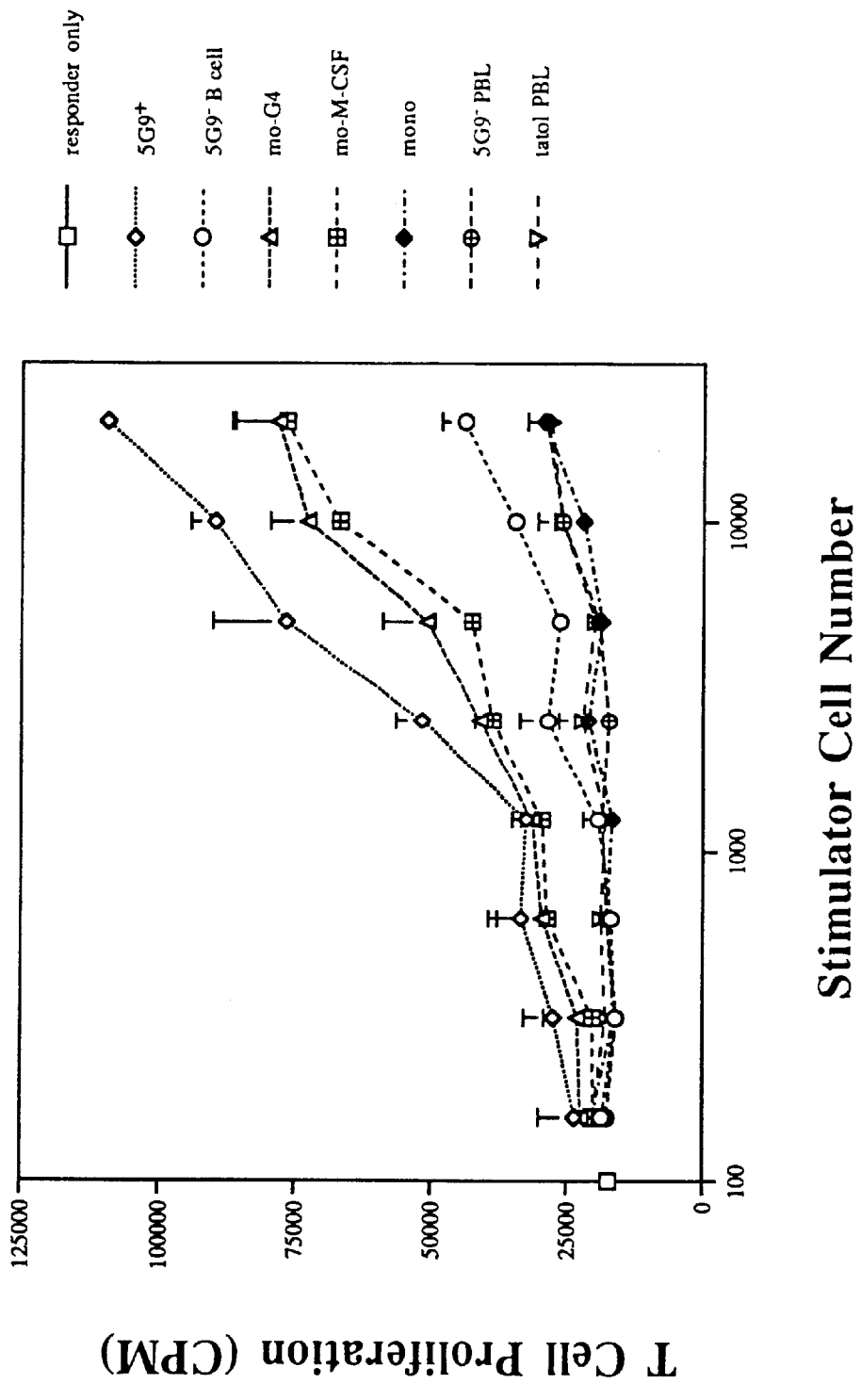
FIG. 15 illustrates MLR stimulation function of 5G9 positive cells.

FIG. 15 illustrates allogeneic MLR stimulation function of 5G9 positive cells. Although DC were named because of their distinctive morphology, this feature is insufficient to define a DC. The ability to induce a potent MLR is a characteristic feature of mature DC. The ability of Dendritic like 5G9$^+$ B cells to induce the proliferation of allogeneic T cells was compared with that of other leukocyte populations, such as total PBMC, monocytes, 5G9$^-$ B cells, 5G9$^-$ blood PBMC, moDC cultured in IL-4 and GM-CSF for 24 h. 5G9$^+$ cells were found consistently to be the most potent allogeneic MLR stimulators.

The novel peripheral blood cell with B cell phenotype plus DC morphology and function presented herein, (a "B-DC cell"), was identified and characterized using mAb 5G9. The mAb 5G9-positive fraction of Dendritic like cells exhibits unique long and thin processes and was shown to be CD19, CD20, CD22, CD40, CD83 (only after positive selection), HLA-Dr$^{hi}$ positive, as well as immunoglobulin $\mu$ chain positive and either kappa- or lambda-light chain positive. They did not express CD3, CD4, CD5, CD10, CD13, CD14, CD15, CD16, CD33, CD56, CD64. Functional study showed these cells to be potent antigen presenting cells in allogeneic mixed lymphocyte reaction (MLR) compared with 5G9$^-$ PBL cells, 5G9$^-$ B cells, monocytes, monocyte-derived DC, and macrophages.

The percentage of 5G9$^+$ DC-like cells in human peripheral blood was studied by flow cytometry analysis of 5G9$^+$ cells in the high light scatter gate and low light scatter gate. The higher HLA-Dr and CD83 expression of 5G9$^+$ cells in the high light scatter gate and the relatively larger cell size of DC-like cells shown in immunohistochemical and Wright-Giemsa of cytospin slides of 5G9$^+$ cells suggested that DC-like cells were in the high light scatter gate. Typically, 5G9$^+$, CD19$^+$ CD3$^-$, CD14$^-$, CD56$^-$ cells in the high light scatter gate represented 0.29±0.06 (n=6) of total mononuclear cells, and about 3% of a B cell subpopulation. Therefore, 5G9$^+$, DC-like B cells represented a trace population of peripheral blood mononuclear cells. Total PBMC were cultured for 4 days in RPMI-1640, 10% FCS and 1000 u/ml IL-4. The flow cytometry analysis of isolated 5G9$^+$ cells from these cultured cells revealed the overlapping of the percentage of CD19$^+$ cells (90%) and percentage of cells with DC morphology studied by immunohistochemical and Wright-Giemsa stain of cytospin slides (64%), thus indicated the B cell phenotype of the DC-like cells. This was also confirmed by immunohistochemical study of cytospin slides of 5G9$^+$ cells of morphologically Dendritic like cells with CD19 and CD21 staining ( data not shown). The marked increase in percentage of DC-like B cells in 5G9$^+$ cells fraction of cultured PBMC compared to uncultured cells (64% vs 4.7%) implied the existence of both B-DC and progenitors of B-DC in PBMC. Upon stimulation by IL-4 or growth factors secreted by other cells during the culture period, the progenitors may have developed into DC-like cells. If mAb and magnetic bead isolated 5G9$^+$ cells were cultured in the same medium for four days, most cells appeared apoptotic as observed by light microscopy and FACS analysis (data not shown), indicating that IL-4 was not the appropriate growth factor for B-DC. The increased B-DC in isolated 5G9$^+$ cells from cultured total PBMC may have been caused by the growth factors secreted by monocytes or other cells in the culture.

Compared to CD19$^+$ and CD21$^+$ cells, only cells isolated with mAb 5G9 were double positive for CD83, further suggesting the correlation of 5G9 antigen and DC-like cells. The high percentage of cells reactive with mouse IgG1 and goat anti-mouse IgG-FITC in the CD19 isolated fraction implies that the mAb remained on the cell surface after the isolation procedure. The low percentage of CD21$^+$ cells in all three fractions suggests that after isolation CD21 antigen was lost from the B cell surface. The negative reaction of 5G9$^+$ cells with goat anti-mouse IgG-FITC and the positive reaction with goat anti-mouse IgG-FITC after incubating with freshly added mAb 5G9 suggests that 5G9 antigen/antibody complexes were completely internalized after overnight culture and 5G9 antigen may quickly return back to the cell surface after unloading the antibody, or a new antigen may be quickly synthesized.

Morphologically, 5G9$^+$, B-DC appear to be most similar to human tonsil folicular dendritic cells (FDC) previously isolated by Hart et al. However, tonsil DC were lineage negative. The lineage relationship of dendritic cells with other haematopoietic cells and within the broader class of DC is not completely defined. DC in different tissue sites and having slightly different characteristics all play a specialized role in maintaining self tolerance by the endocytosis and presentation of antigens within their environment. Recent evidence now suggests a possible lineage relationship between T cells and lymphoid dendritic cells and like B-DC also appears to conflict with the view that dendritic cells have a common origin with myeloid cells. One possibility is that dendritic cells mature in different tissue sites from bone marrow derived precursors and develop region specific characteristics which could reflect lineage differences.

A recent working definition of blood DC emphasized "a cell-surface Ag phenotype distinguishing it from other leukocytes, notably Mo/Mφ and B lymphocytes". The most current separation procedures of blood DC are also based on the lineage-negative feature of DC. Aspects of the present invention, specifically the identification of DC-like cells with B cell surface Ag phenotype appears to conflict with current definitions of DC. The DC-like B cells described herein possess consensus DC properties and characteristics; the distinctive morphology; the potent ability to stimulate allogeneic T cell proliferation; marked cell motility; active membrane extension and retraction, and the expression of certain DC-associated Ags such as CD83, HLA-Dr$^{hi}$. While not wishing to be bound by theory, these properties would appear to lead to the conclusion that B-DC are a previously unrecognized member of the DC family. While not wishing to be bound by theory, there appears to be a close relationship of DC and B-cells and the possibility that B cells can be morphologically and functionally differentiated to DC.

Figure 16:
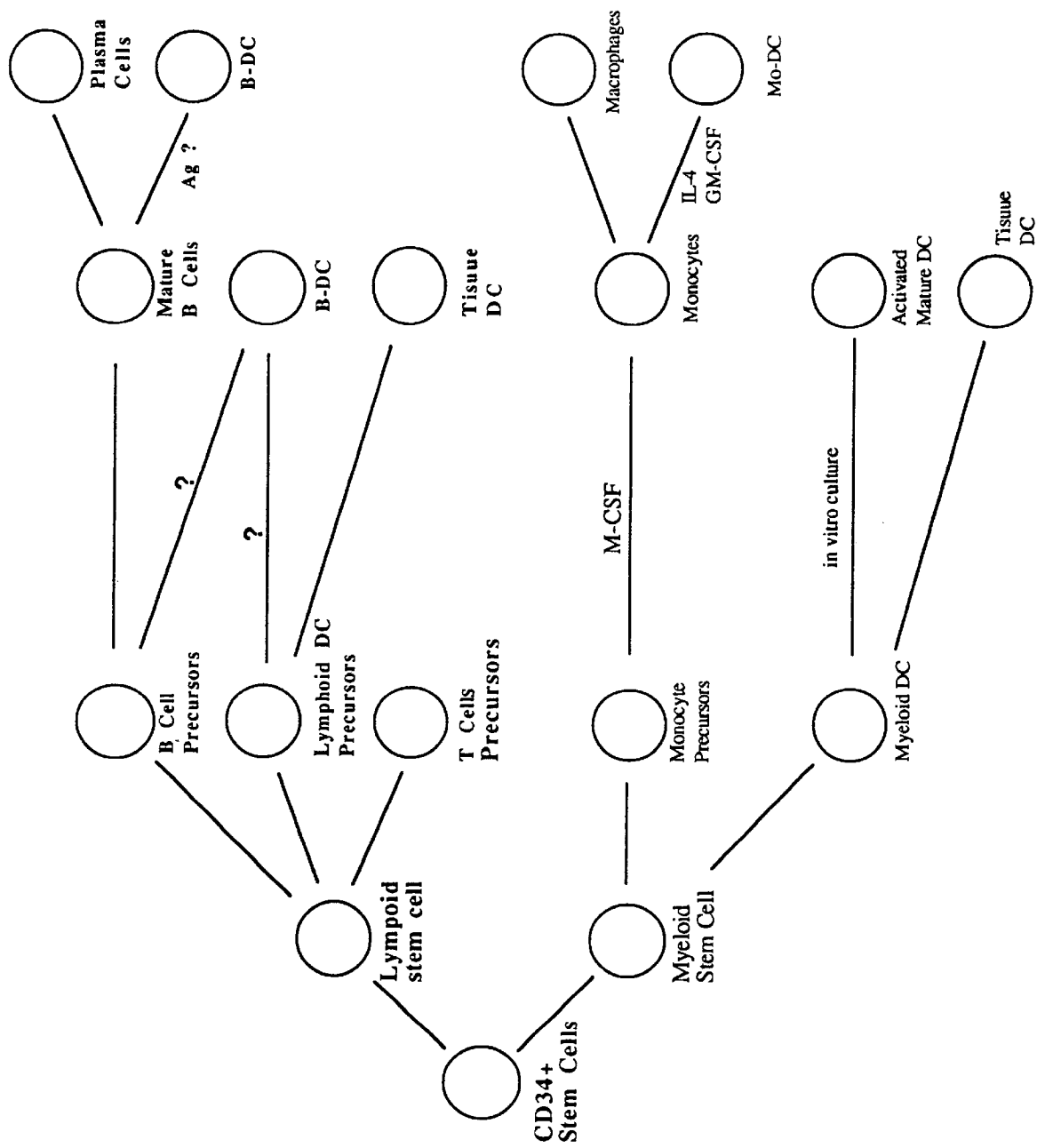
FIG. 16 shows a suggested hematopoietic differentiation pathway for DC-like B cells or B-DC compare to myeloid DC differentiation. Three possible pathways are shown: mature B cells to B-DC; B cell precursor to B-DC; lymphoid DC precursor to B-DC.

This classic pathway of B cell development, and the separation of circulating DC-like cells from the blood B cell fraction discussed herein, suggest that two separate outcomes may evolve during B cell development. A fraction of B cells, which might be a fraction of memory B cells after stimulation by antigen, may develop into DC. With antigen-specific Igs on their surface and class II HLA expression, these cells may be very efficient antigen specific professional antigen presenting cells, and function as positive feedback cells to stimulate further T cell proliferation and subsequent antibody specific B cell proliferation, and thus produce a more profound immune response. While not wishing to be bound by theory, a suggested hematopoietic differentiation pathway for DC-like B cells or B-DC compared to myeloid DC differentiation is showed in FIG. 16. This proposed pathway suggests that B cells can develop into plasma cells and B-DC. There are three possible pathways: mature B cells to B-DC; B cell precursor to B-DC; lymphoid DC precursor to B-DC. It is hypothesized herein based on the experimental data that B-DCs can develop from mature B cells.

While the foregoing has been set forth in considerable detail, the embodiments, procedures and compositions are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein.

What is claimed is:

1. Isolated antigen presenting cells having dendritic cell properties and characteristics wherein said cells are nonadherent to tissue culture plastic and are reactive with monoclonal antibody 5G9 (mAb5G9), wherein said mAb5G9 is produced by a hybridoma designated 5G9 having an A.T.C.C. Accession Number of HB-12430.

2. The isolated cells of claim 1, wherein said cells express the phenotype CD19+, CD20+, CD40+, CD83+, HLA-DR-hi positive, immunoglobulin μ chain positive, Kappa light chain positive, lambda-light chain positive, CD3−, CD4−, CD5−, CD10−, CD13−, CD14−, CD15−, CD16−, CD33−, CD56−, and CD64−.

3. A method of isolating cells having a dendritic like morphology comprising:

obtaining a sample which contains said cells having a dendritic like morphology;

mixing the sample with monoclonal antibody 5G9 (mAb 5G9), which is capable of reacting with an antigen expressed by the dendritic like cell, wherein said mAb 5G9 is produced by a hybridoma designated 5G9 having an A.T.C.C. Accession Number of HB-12430; and selecting the cells so as to separate from the sample a purer population of cells having a dendritic cell morphology and which are nonadherent to tissue culture plastic.

* * * * *